United States Patent
Shen et al.

(10) Patent No.: US 11,582,957 B2
(45) Date of Patent: Feb. 21, 2023

(54) TDP-43 KNOCK-IN MOUSE MODEL OF AMYOTROPHIC LATERAL SCLEROSIS

(71) Applicant: Academia Sinica, Taipei (TW)

(72) Inventors: Che-Kun James Shen, Taipei (TW); Shih-Ling Huang, Yunlin County (TW)

(73) Assignee: ACADEMIA SINICA, Taipei (TW)

( * ) Notice: Subject to any disclaimer, the term of this patent is extended or adjusted under 35 U.S.C. 154(b) by 764 days.

(21) Appl. No.: 16/387,430

(22) Filed: Apr. 17, 2019

(65) Prior Publication Data

US 2019/0335727 A1    Nov. 7, 2019

Related U.S. Application Data

(60) Provisional application No. 62/665,590, filed on May 2, 2018.

(51) Int. Cl.
| | | |
|---|---|---|
| *A01K 67/027* | (2006.01) | |
| *A61K 49/00* | (2006.01) | |
| *C07K 14/47* | (2006.01) | |
| *C12N 5/0793* | (2010.01) | |
| *G01N 33/564* | (2006.01) | |
| *G01N 33/50* | (2006.01) | |

(52) U.S. Cl.
CPC ...... *A01K 67/0278* (2013.01); *A61K 49/0008* (2013.01); *C07K 14/4703* (2013.01); *C12N 5/0619* (2013.01); *G01N 33/5023* (2013.01); *G01N 33/564* (2013.01); *A01K 2217/072* (2013.01); *A01K 2227/105* (2013.01); *A01K 2267/0318* (2013.01); *C12N 2506/02* (2013.01)

(58) Field of Classification Search
CPC ............ A01K 67/0278; A01K 67/0275; A01K 2217/072; A01K 2267/0318
See application file for complete search history.

(56) References Cited

U.S. PATENT DOCUMENTS

| | | |
|---|---|---|
| 6,245,963 B1 | 6/2001 | Li et al. |
| 7,745,683 B2 | 6/2010 | Riken |
| 2011/0321179 A1* | 12/2011 | Kabashi ............. C12N 15/8509 800/3 |

OTHER PUBLICATIONS

Johnson (JBC, 284(30): 20329-20339, 2009 (Year: 2009).*
Kabashi (Nat Genet, 40: 572-574, 2008) (Year: 2008).*
Wichterle, (Cell, 110, Abstract, 2002). (Year: 2002).*
Wu (The Journal Of Biological Chemistry vol. 287, No. 33, pp. 27335-27344, Aug. 10, 2012) (Year: 2012).*
Jo (Experimental & Molecular Medicine (2020) 52:1652-1662) (Year: 2020).*
Nonaka, ( Hum. Mol. Genet. 18, 3353-3364 (2009) (Year: 2009).*

* cited by examiner

*Primary Examiner* — Valarie E Bertoglio
(74) *Attorney, Agent, or Firm* — Hsiu-Ming Saunders; Intellectual Property Connections Inc.

(57) ABSTRACT

The invention relates to a genetically modified mouse comprising a heterozygous mutation of Tardbp (TDP-43) gene in that the Asn at amino acid 390 in TDP-43 is substituted with an amino acid that is different from Asn, wherein the genetically modified mouse exhibits Amyotrophic lateral sclerosis (ALS)-like phenotypes, TDP-43 proteinopathies and/or motor neuron degeneration. The invention also so relates to an isolated spinal cord motor neuron differentiated from an embryonic stem cell (ESC) that is obtained from an offspring of a genetically modified mouse according to the invention. Methods for identifying an agent alleviating and/or suppressing ALS-TDP pathogenesis are also disclosed.

20 Claims, 18 Drawing Sheets

Specification includes a Sequence Listing.

FIG. 1A
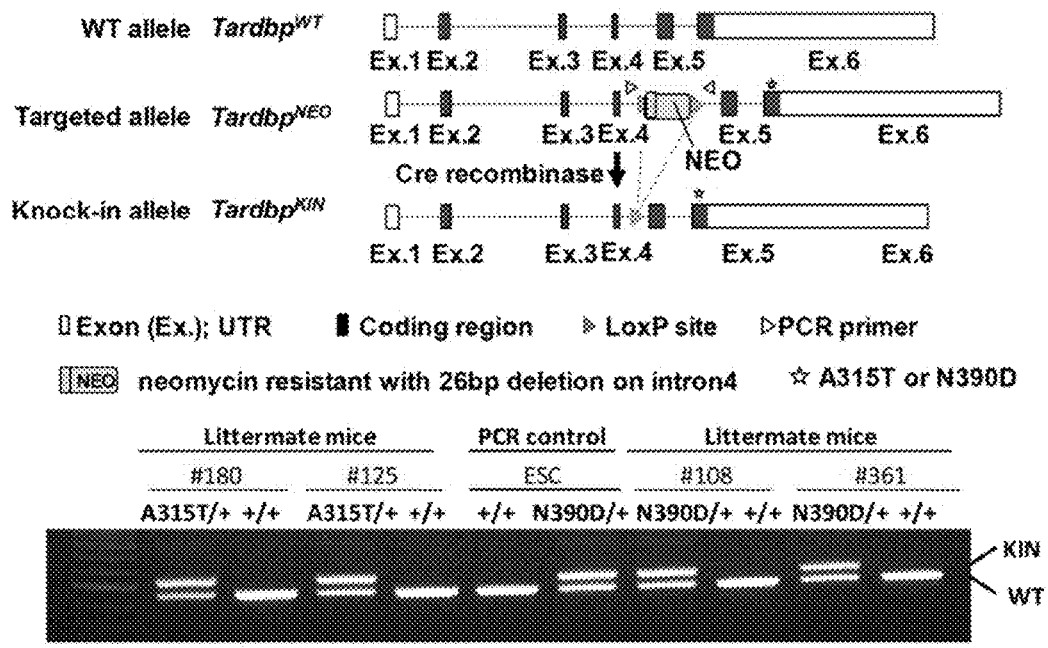
FIG. 1B-(a)
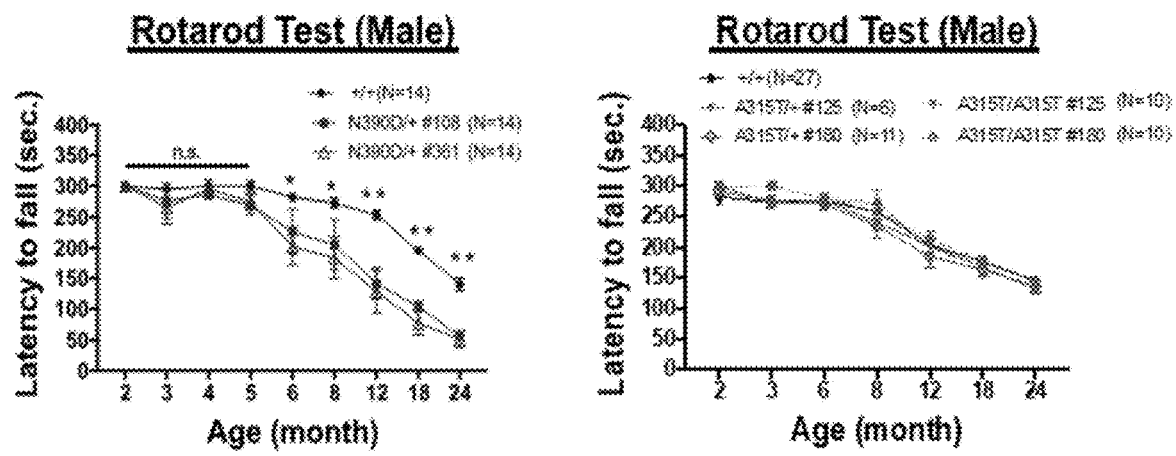
FIG. 1B-(b)
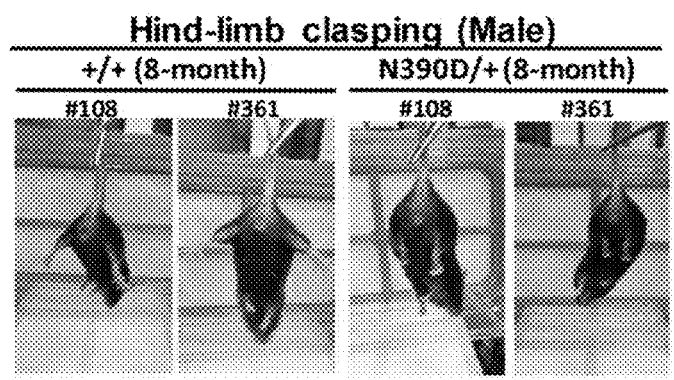

FIG. 1C
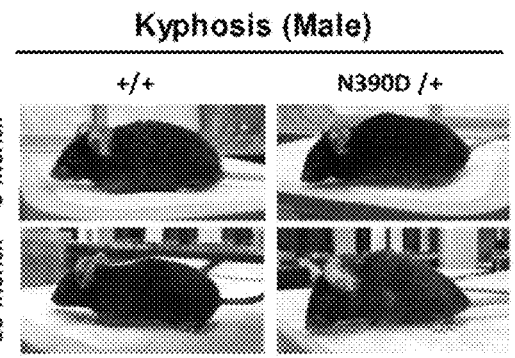
FIG. 1D-(a)
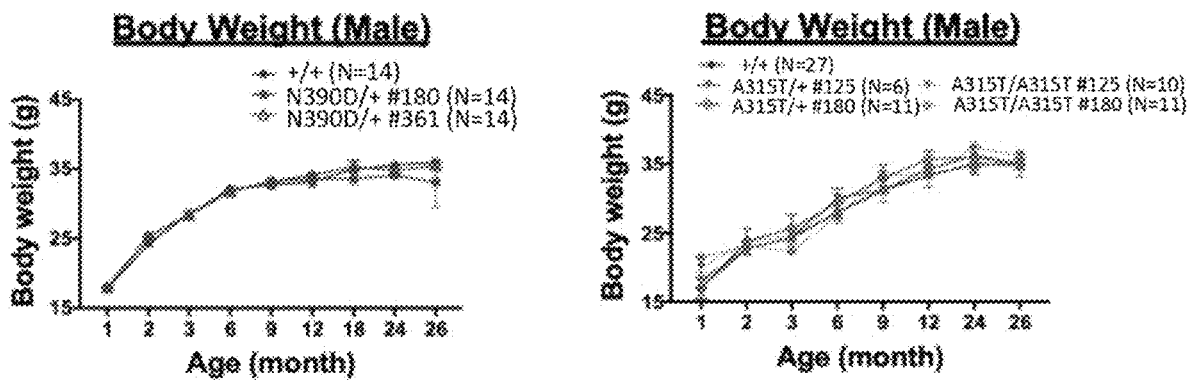
FIG. 1D-(b)
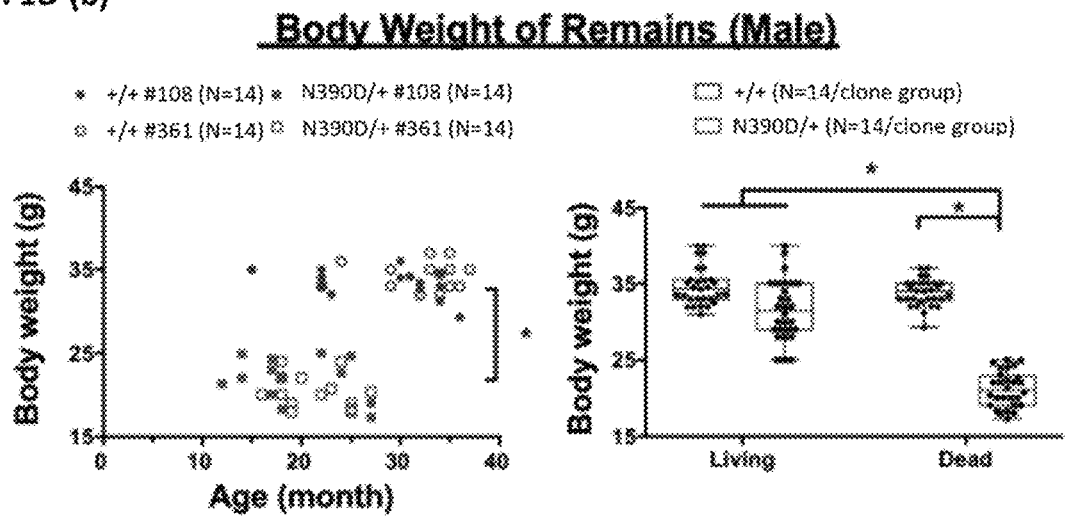

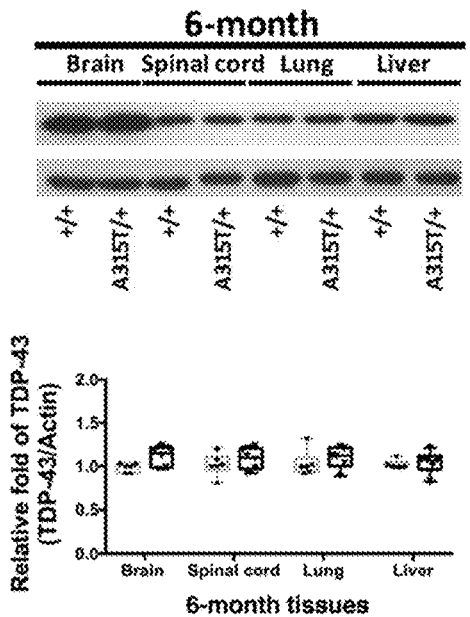
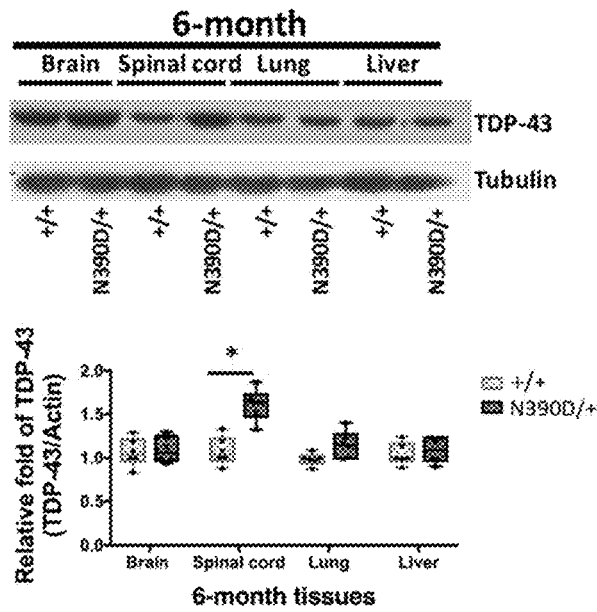
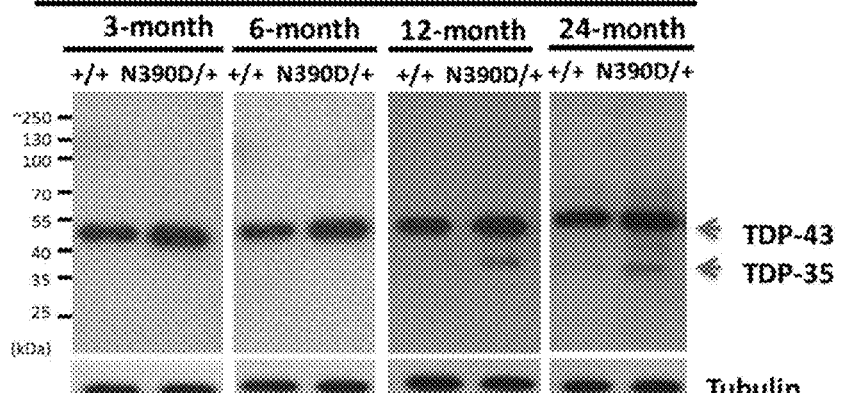
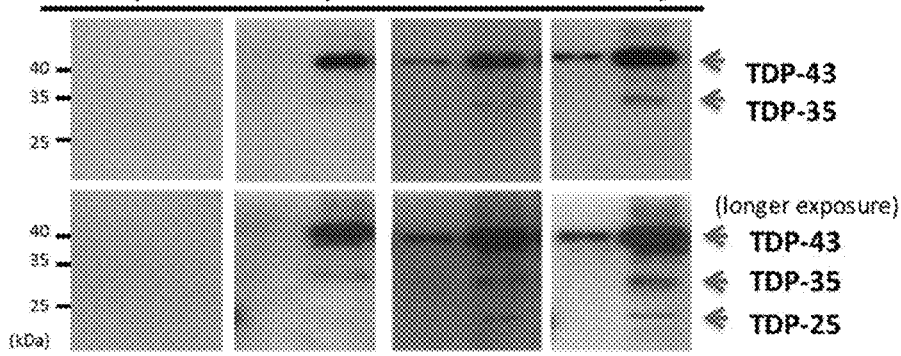

FIG. 2B-(b)
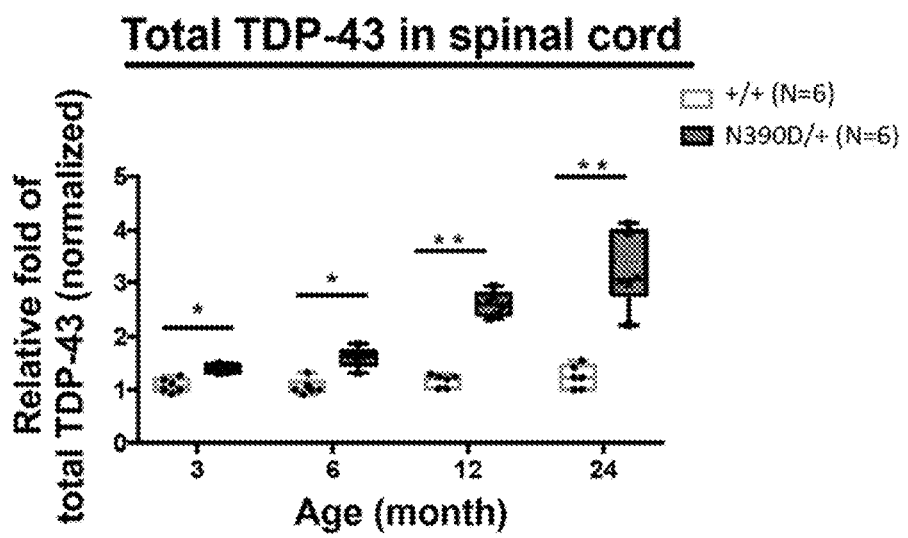
FIG. 2B-(c)
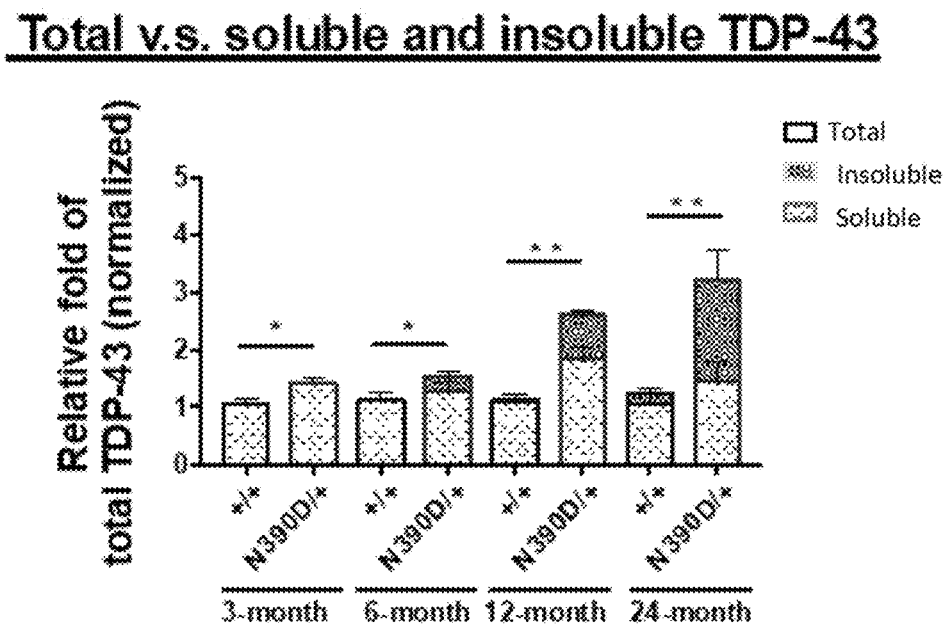
FIG. 2B-(d)
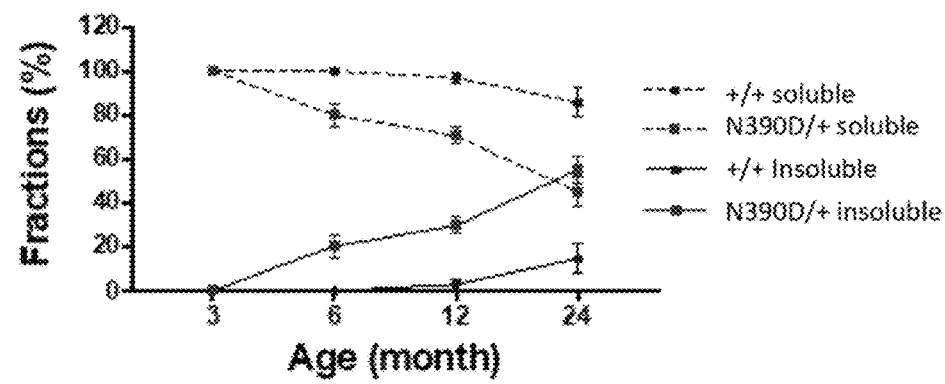

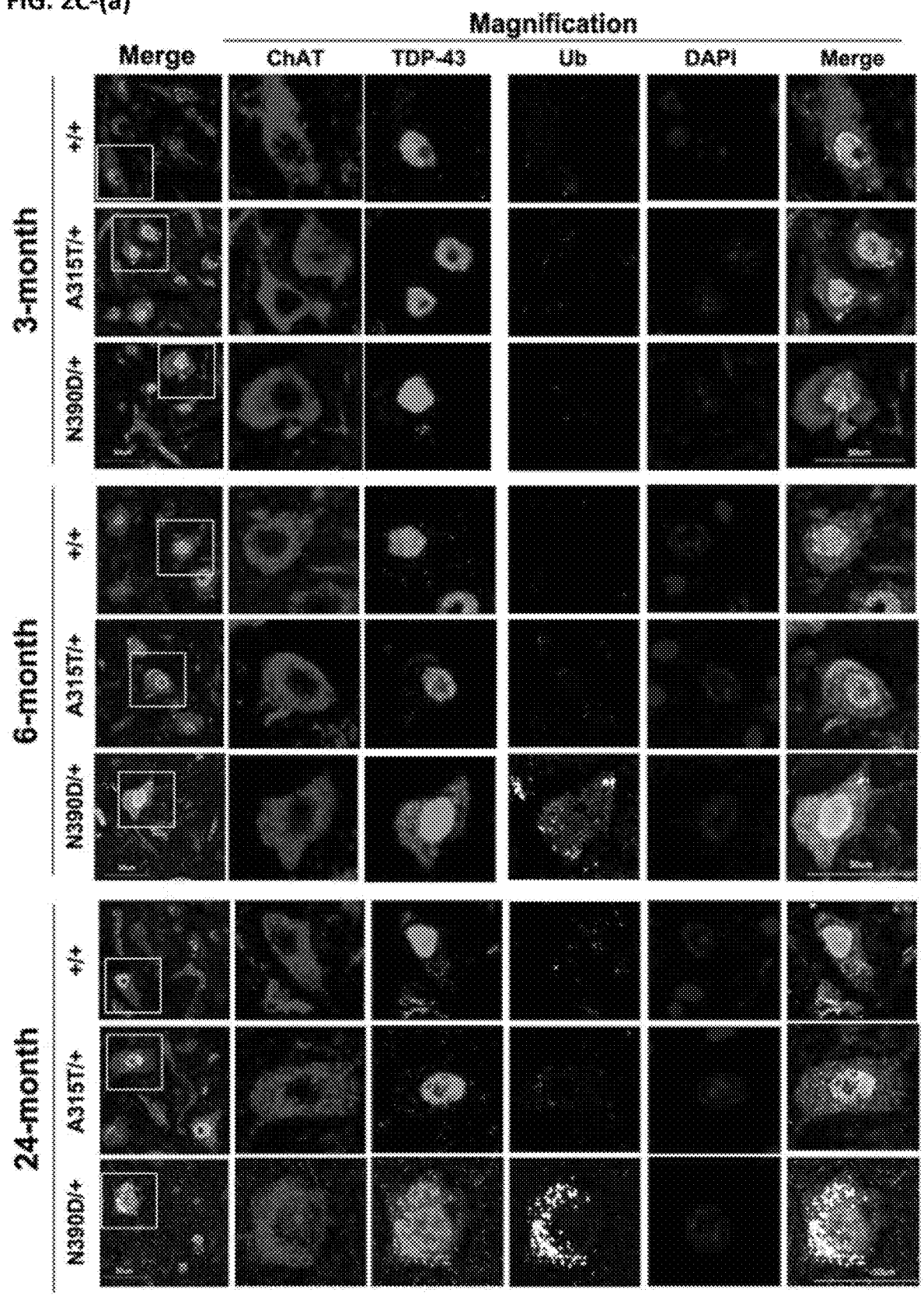
FIG. 2C-(a)

FIG. 2C-(b)
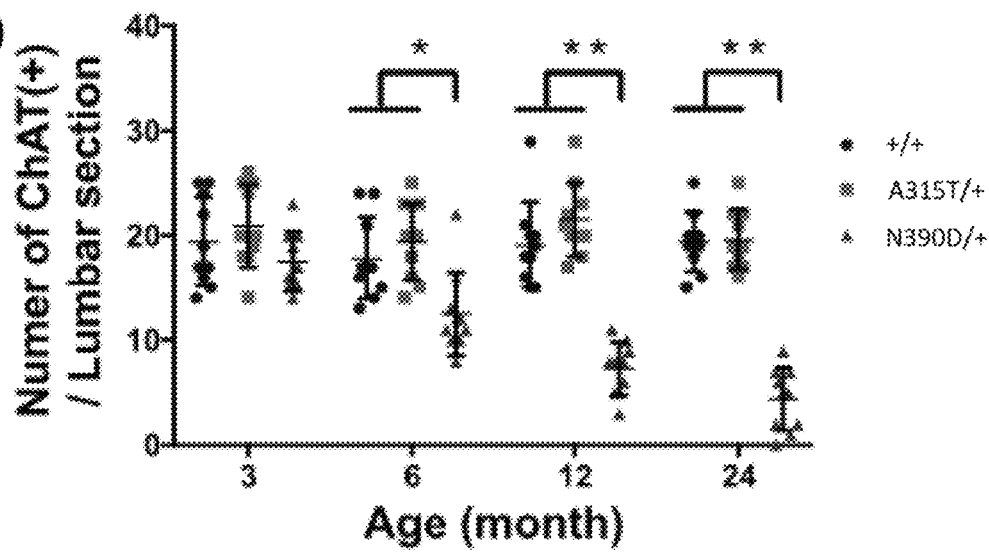
FIG. 2C-(c)
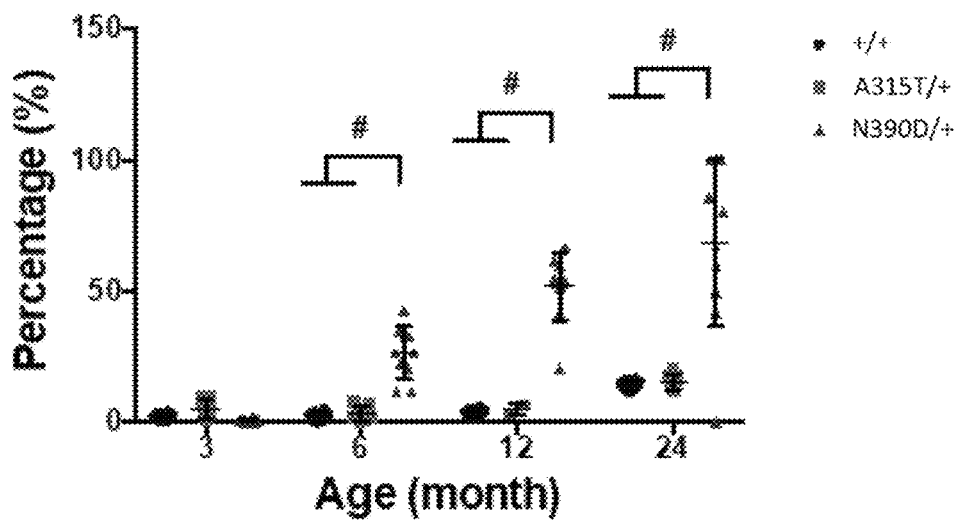
FIG. 2C-(d)
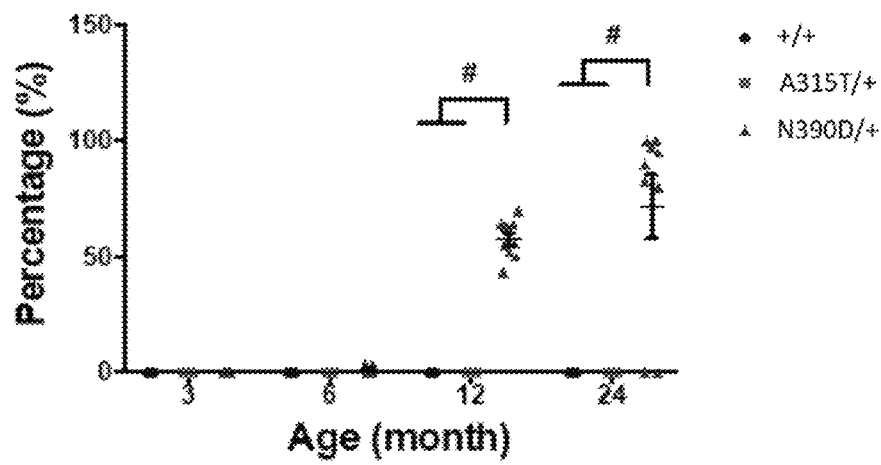

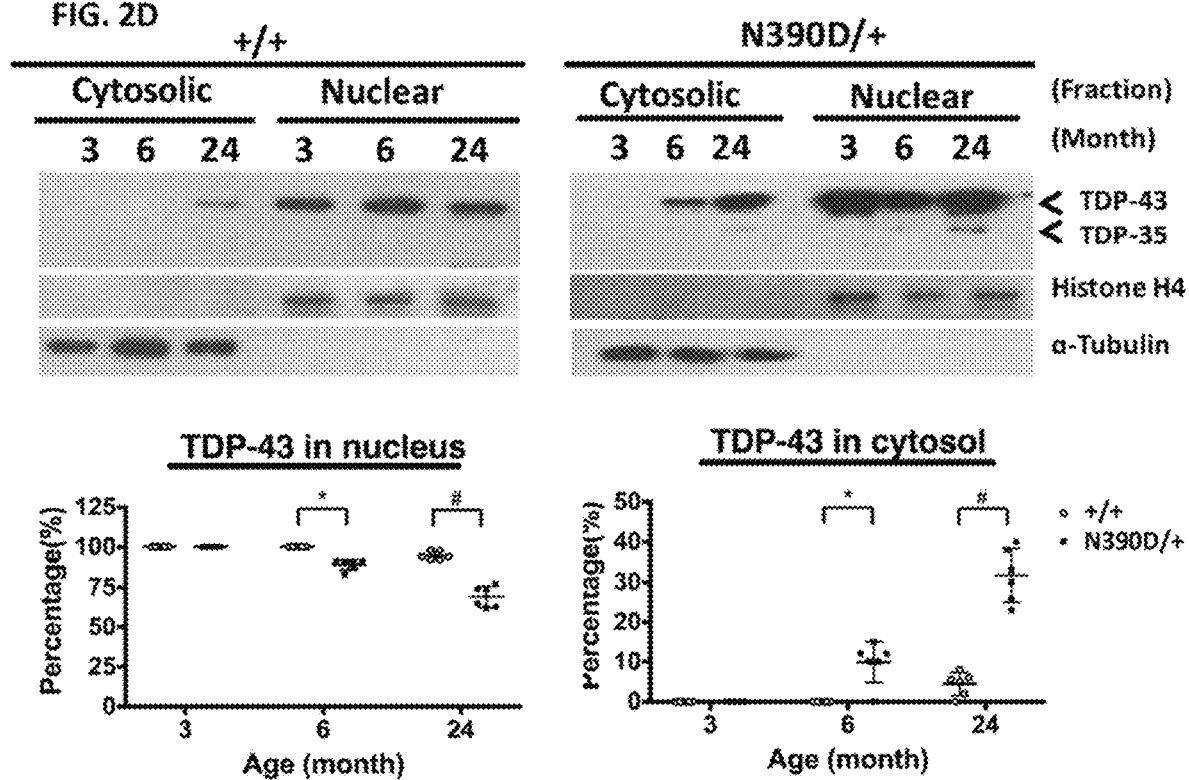
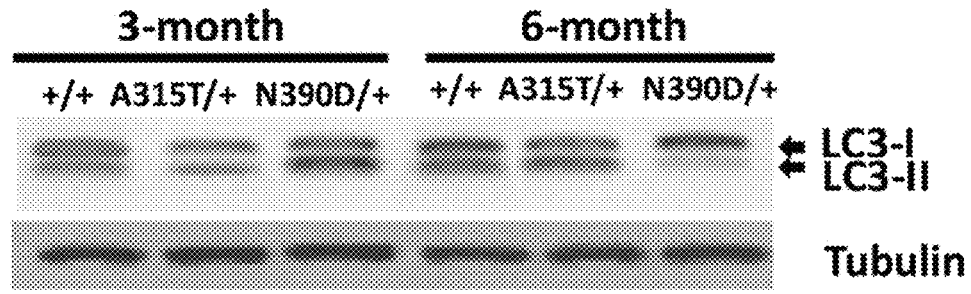
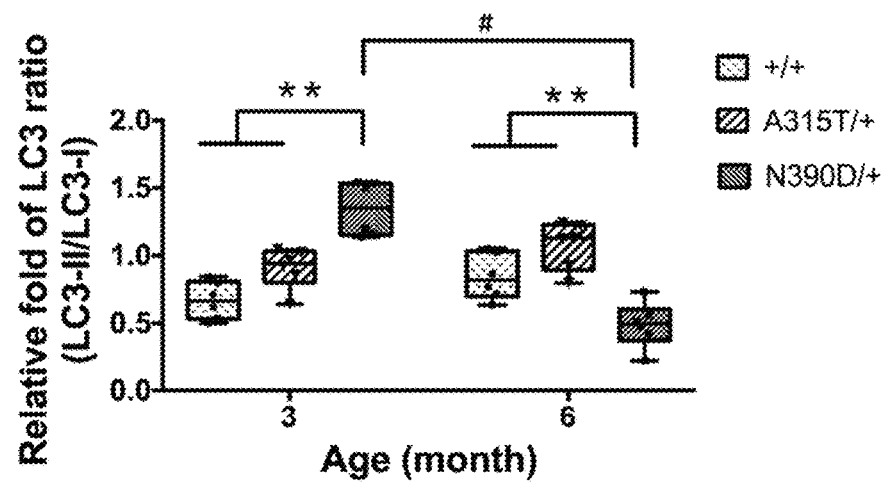

FIG. 3B
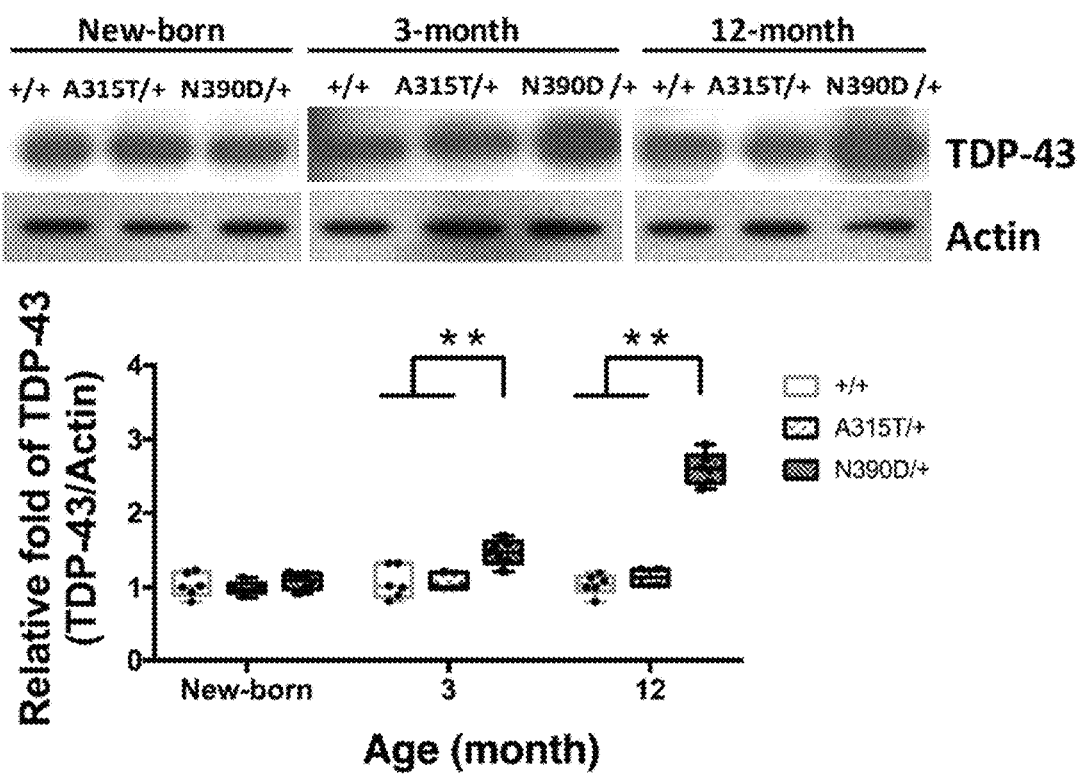
FIG. 3C-(a)
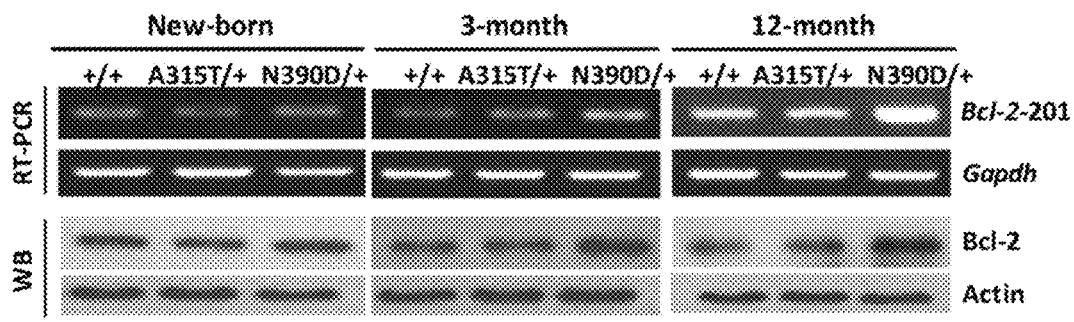

FIG. 3C-(b)
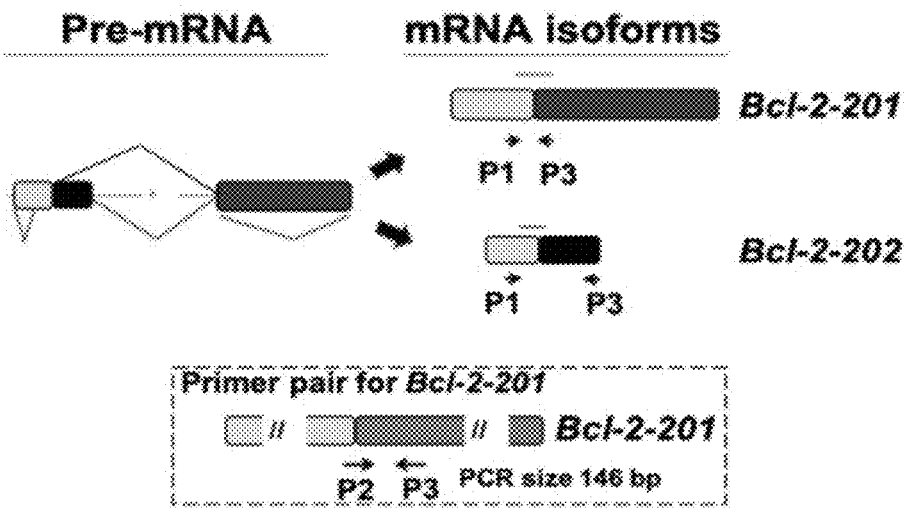
FIG. 3C-(c)
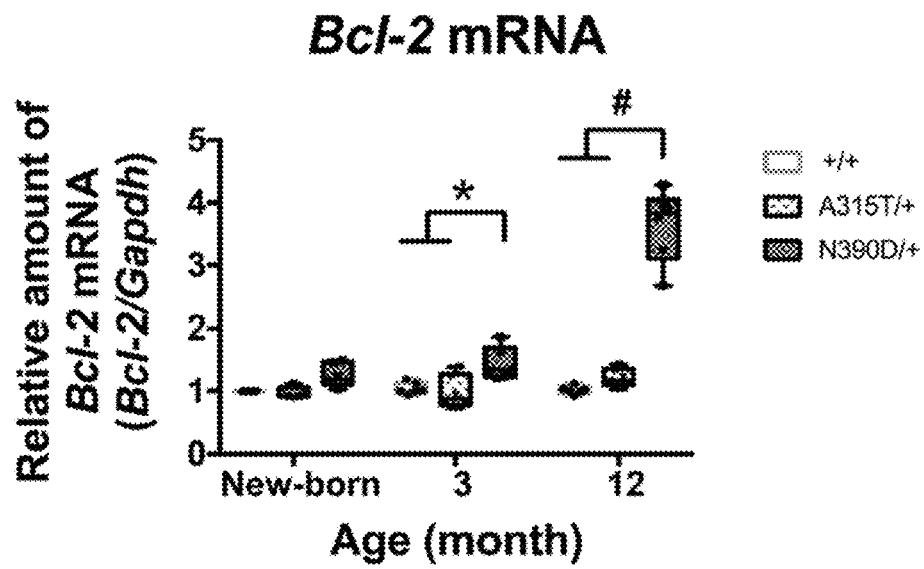
FIG. 3C-(d)
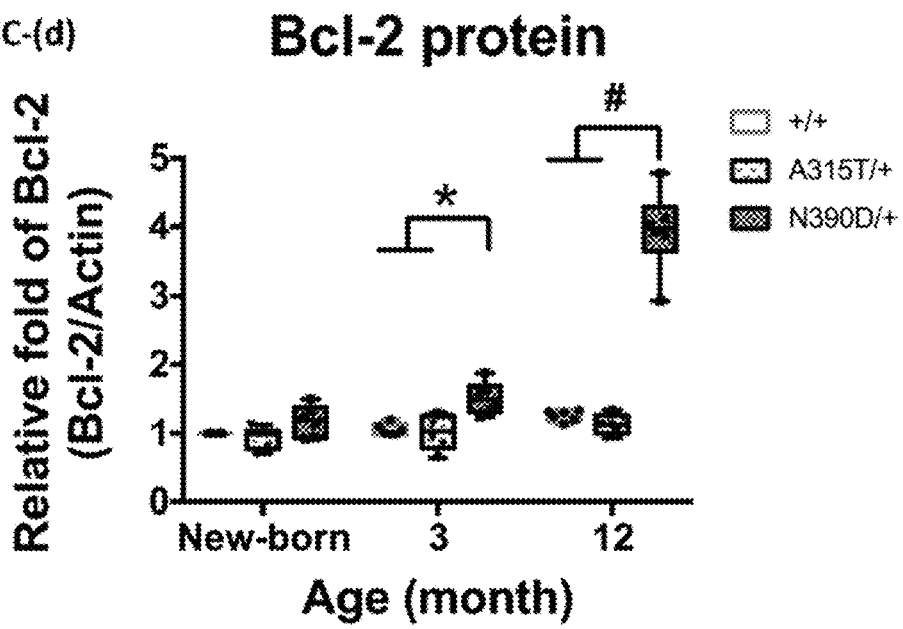

FIG. 3D
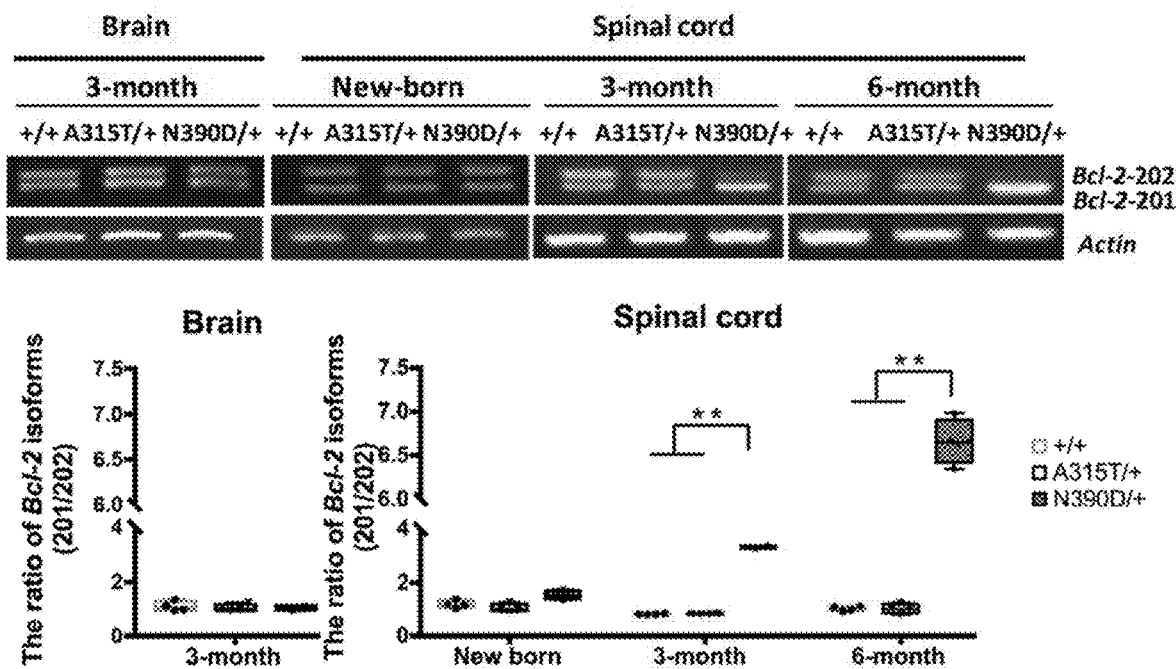
FIG. 3E-(a)
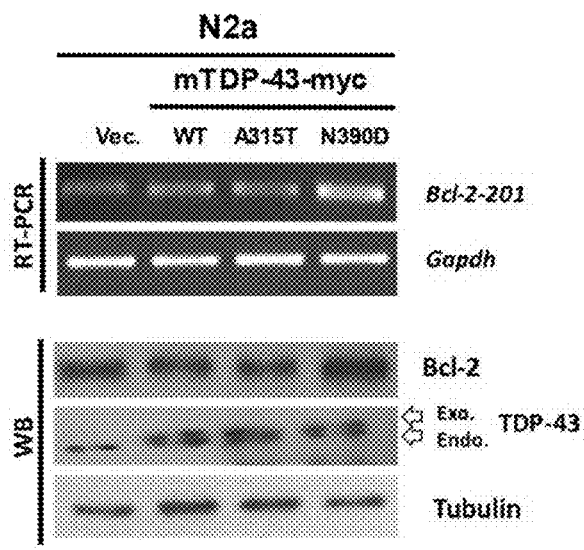
FIG. 3E-(b)
FIG. 3E-(c)
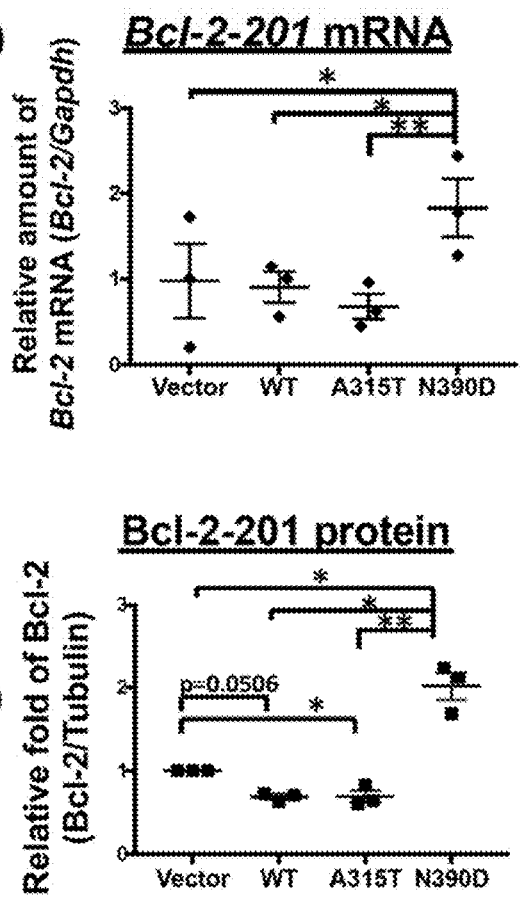

FIG. 4B-(a)
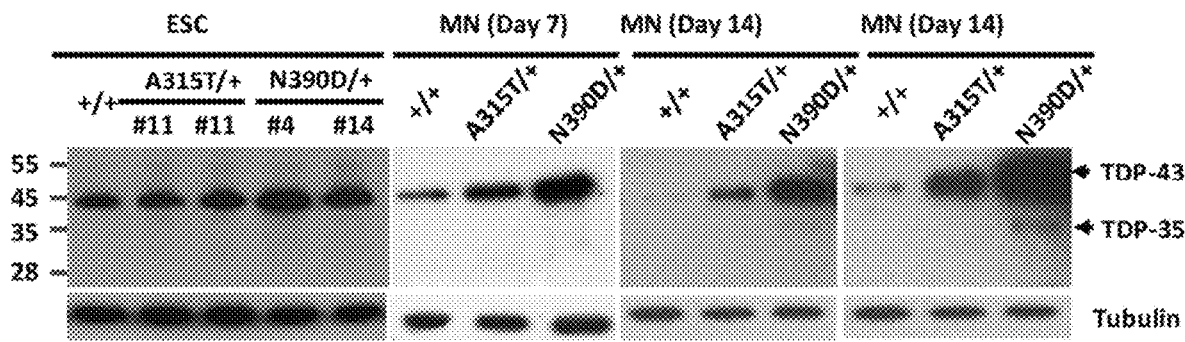
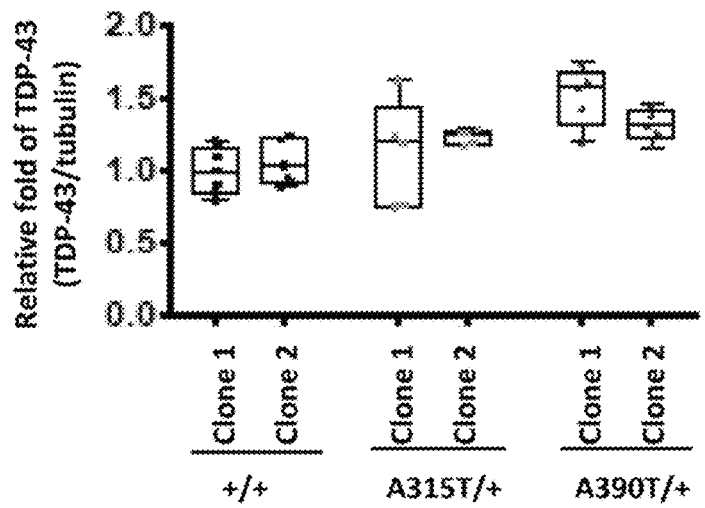
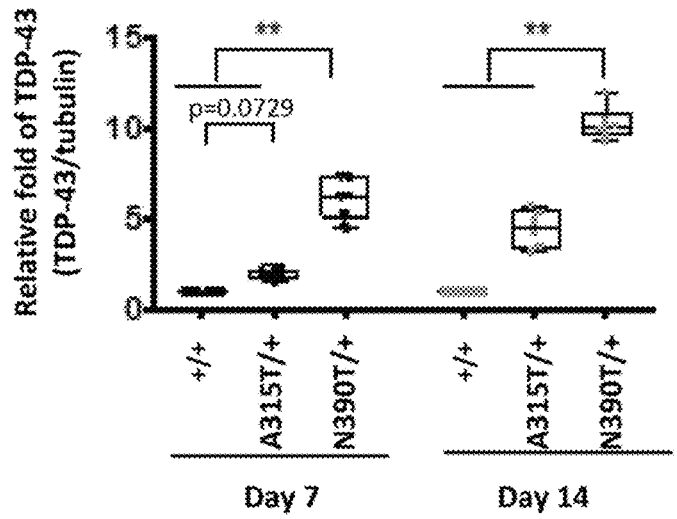

FIG. 4B-(b)
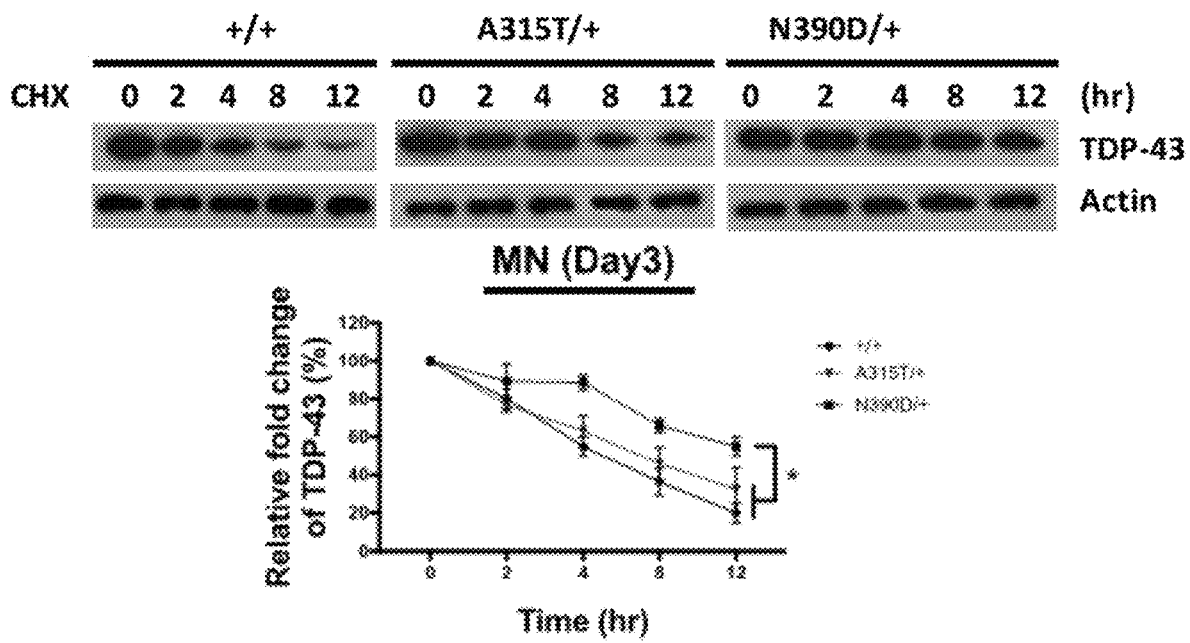
FIG. 4C
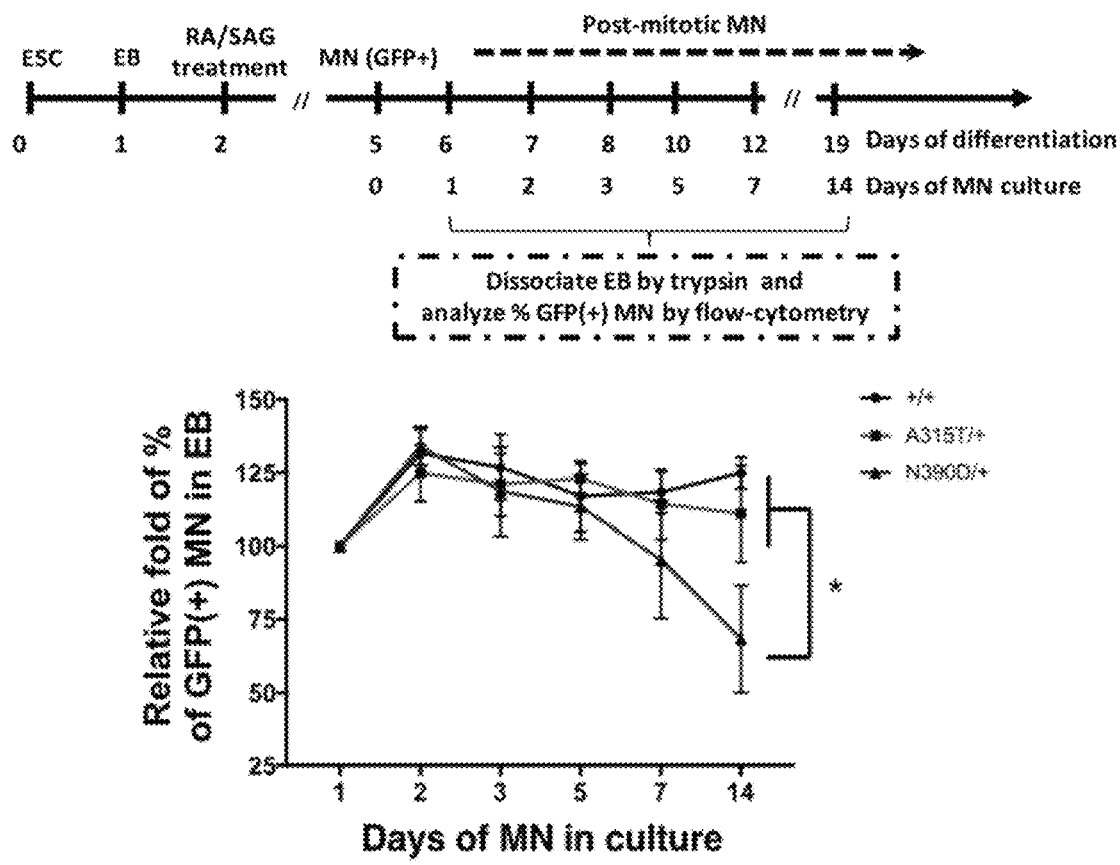

FIG. 4D-(a)
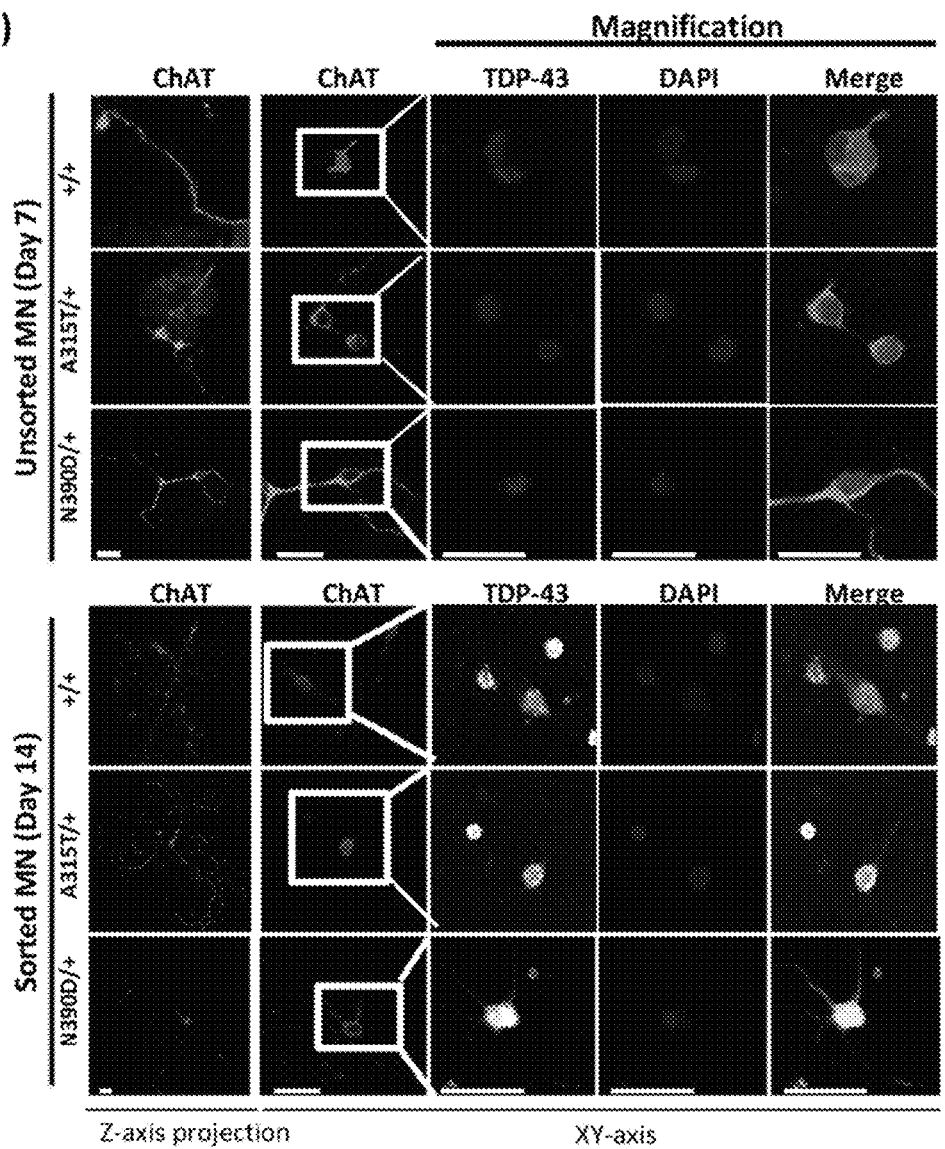
FIG. 4D-(b)
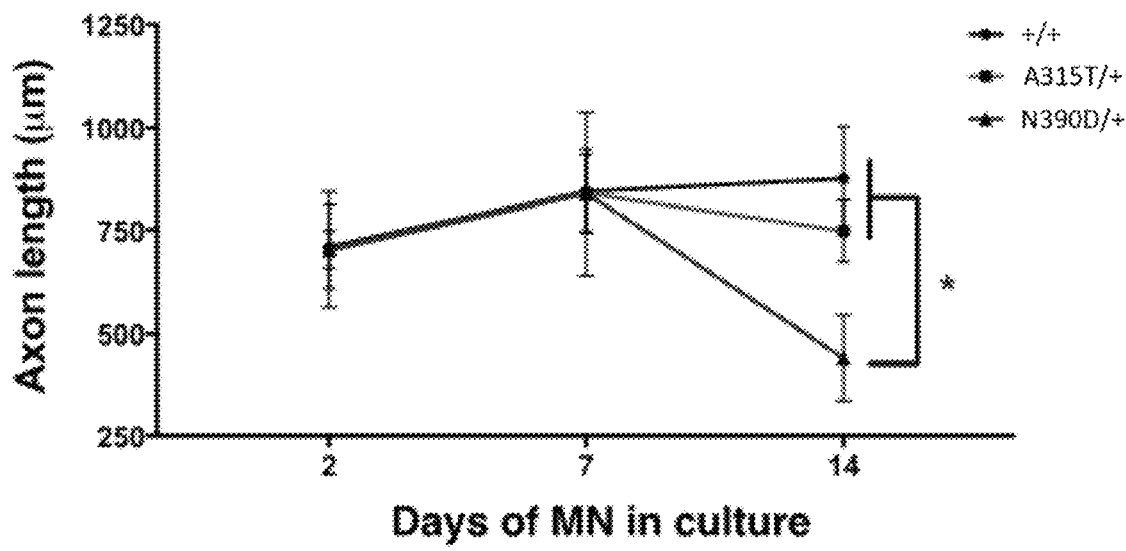

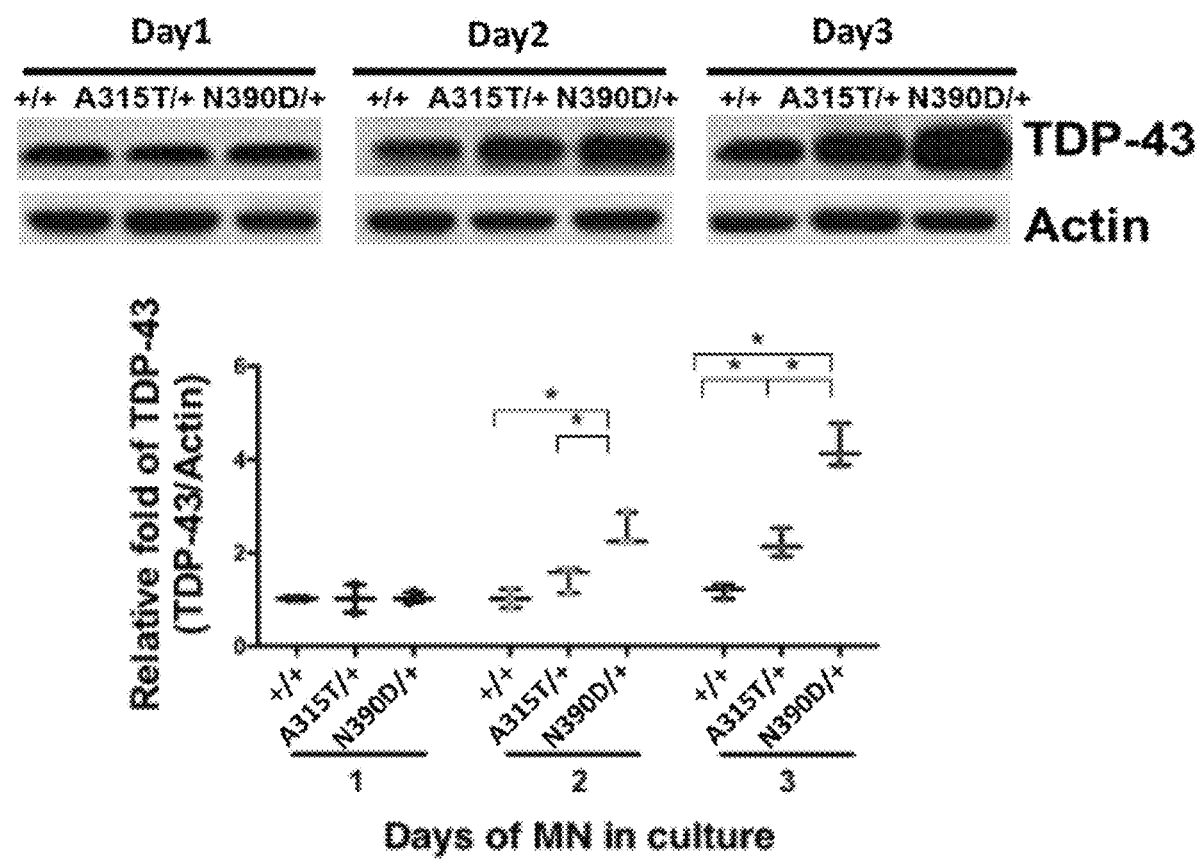
FIG. 5A-(a)

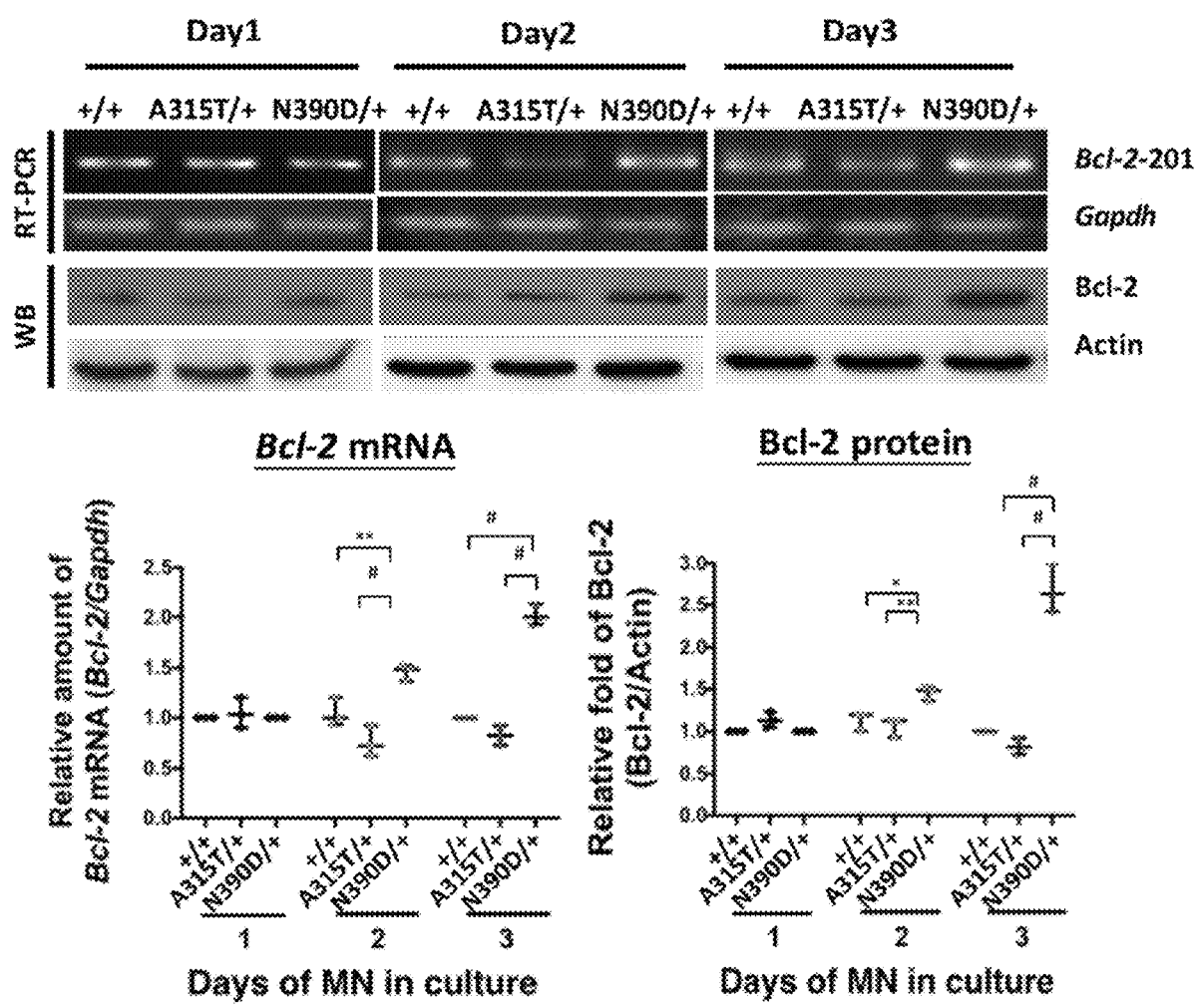
FIG. 5A-(b)

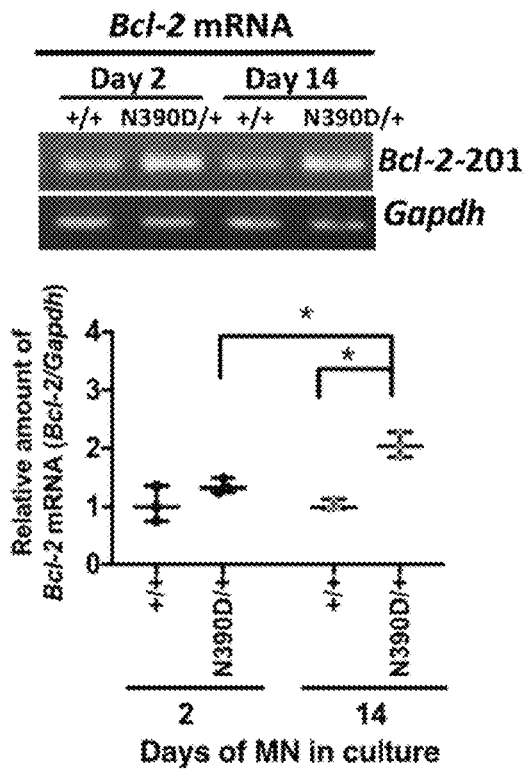
FIG. 5B-(a)
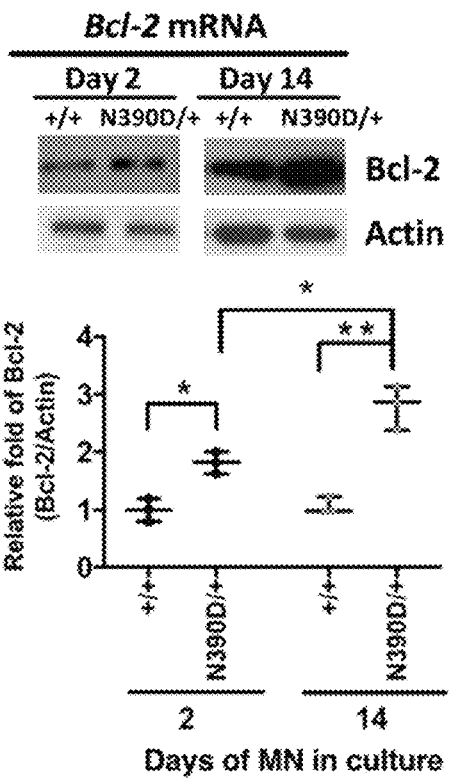
FIG. 5B-(b)
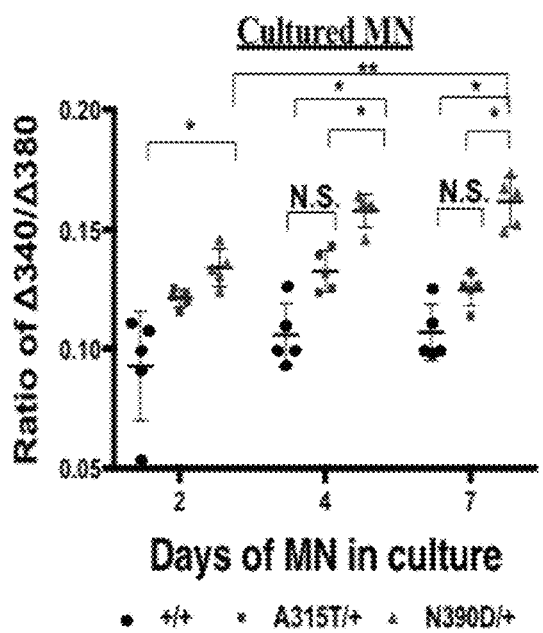
FIG. 5C-(a)
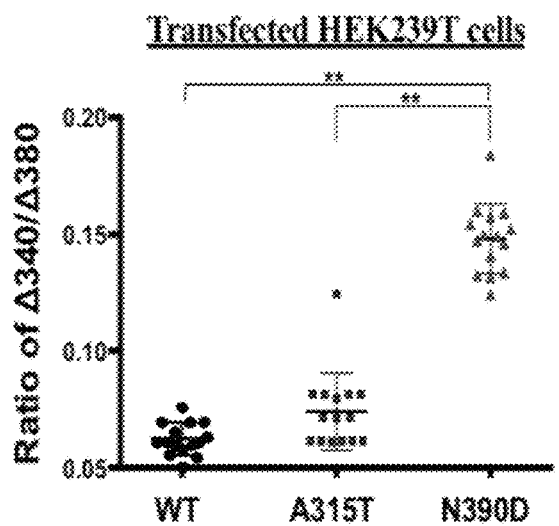
FIG. 5C-(b)

TDP-43 KNOCK-IN MOUSE MODEL OF AMYOTROPHIC LATERAL SCLEROSIS

FIELD OF THE INVENTION

The present invention relates to the field of amyotrophic lateral sclerosis (ALS).

BACKGROUND OF THE INVENTION

While the genetic basis of 80% of ALS is unknown, at least 31 genes, including SODI and TARDBP encoding the RNA/DNA-binding protein-TDP-43, with mutations associated with ALS have been identified. A total of more than 50 missense mutations have been identified in the TARDBP gene through genetic analysis of several familial and sporadic ALS cases. Significantly, more than 95% of all ALS patients (ALS-TDP) are characterized by enhanced cleavage to generate TDP-35/TDP-25 fragments, by accumulation of ubiquitinated TDP-43, and by formation of ubiquitin (+), TDP-43(+) aggregates in the cytosol.

TDP-43 is a ubiquitously expressed heterogeneous nuclear ribonucleoprotein (hnRNP) protein that localized primarily in the nucleus and required for multiple cellular pathways including RNA metabolism and translation. Given these ubiquitous functions, aberrant expression of TDP-43 is likely to lead to multiple pathological consequences. Indeed, depletion of TDP-43 results in early embryonic lethality in mice, promotes cellular deficits such as the impairment of autophagy through down-regulation of ATG7 and alteration of fat metabolism via suppression of Tbc1d1, and causes ALS-like phenotypes in mice. Furthermore, under pathologic conditions, the total amount of TDP-43 in the diseased cells is elevated in addition to its mislocalization in the cytosol and abnormal processing as mentioned above. As the pathological consequences of abnormally high levels of TDP-43, the biogenesis of many RNAs required for neural development and synaptic function are impaired. Mutations in TDP-43 also affect the translation of Futsc/MAP1B mRNA in motor neurons and regulate neuronal mRNA trafficking.

In order to study ALS-TDP disease mechanisms, several animal models have been developed which display abnormal expression of TDP-43, either a decrease or increase compared to the wild type mice. Thus far, all studies focusing on the pathological role(s) of mutant TDP-43 have been based on overexpression approaches. Indeed, the transgenic mouse models that overexpress mutant TDP-43 under different neuronal promoters exhibited MND-like phenotype or cognition deficits with neuronal loss, and the hallmarks of TDP-43 proteinopathies. This included mislocalizaiton of nuclear TDP-43, abnormal post-translational modifications, and formation of insoluble ubiquitin (+)/TDP-43 (+) inclusions. Unfortunately, however, overexpression of wild type TDP-43 can also cause FTLD-TDP-like or ALS-like pathogenesis of the transgenic mice. It is therefore difficult to assess the pathological effects of the ALS-associated mutations of TDP-43 compared to wild type TDP-43 without appropriate control of their levels of overexpression, in transgenic animals or in transfected cell culture. White et al. recently reported the construction of a mouse model by homologous knock-in of ALS-FTD associated TDP-43 mutation, Q331K, which exhibited a subtle ALS-FTD like phenotype.

A previously unaddressed need exists in the art to address aforementioned deficiencies and inadequacies, especially in connection with ALS-TDP animal model.

SUMMARY OF THE INVENTION

In one aspect, the invention relates to a genetically modified mouse comprising a heterozygous mutation of Tardbp (TDP-43) gene in that the Asn at amino acid 390 in TDP-43 is substituted with an amino acid that is different from Asn, wherein the genetically modified mouse exhibits Amyotrophic lateral sclerosis (ALS)-like phenotypes, TDP-43 proteinopathies and/or motor neuron degeneration.

In one embodiment, the genetically modified mouse model of the invention exhibits a genotype of N390D/+.

In another embodiment, the genetically modified mouse model of the invention is male.

In another embodiment, the genetically modified mouse model of the invention exhibits motor dysfunction.

In another embodiment, the genetically modified mouse model of the invention further exhibits one or more of the following ALS-like phenotypes: (a) abnormal hind limb-clasping; (b) kyphosis; (c) shorter life span than a wild type mouse; and (d) a weight loss.

In another aspect, the invention relates to a bodily part of the genetically modified mouse of the invention.

In one embodiment, the bodily part of the invention is at least one selected from the group consisting of a cell, a tissue and an organ.

In another embodiment, the genetically modified mouse of the invention is a knock-in mouse, whose genome carries a TDP-43 gene single mutation at nucleotide A at position 1168 of the TDP-43 gene coding sequence (cDNA).

In another embodiment, the genome of the knock-in mouse according to the invention is characterized by a feature that the nucleotide A at the position 1168 of its TDP-43 gene coding sequence is substituted with nucleotide G.

Further in another embodiment, the spinal cord of the genetically modified mouse according to the invention exhibits one or more of the following molecular and cellular pathology as compared to a wild type (+/+) mouse: (a) an increased expression of TDP-43 protein; (b) an enhanced cleavage of TDP-43; and (c) an increased fraction of insoluble TDP-43/TDP-35/TDP-25; (d) mislocalization of TDP-43 from nuclei to cytoplasm of spinal cord motor neurons; (e) accumulation of ubiquitinated TDP-43 proteins in spinal cord motor neurons; and (f) a loss of spinal cord motor neurons.

Further in another aspect, the invention relates to an isolated spinal cord motor neuron differentiated from an embryonic stem cell (ESC) that is obtained from an offspring of a genetically modified mouse according to the invention.

In one embodiment, the offspring results from a cross between the genetically modified mouse and a genetically modified mouse with a genotype of Hb9:GFP.

In another embodiment, the isolated spinal cord motor neuron according to the invention exhibits a genotype of N390D/+.

In another embodiment, the motor neuron expresses GFP under the control of the spinal cord motor neuron-specific promoter Hb9.

Further in another embodiment, an isolated spinal cord motor neuron according to the invention exhibits a higher amount of TDP-43 than a wild type (+/+) motor neuron.

Further in embodiment, an isolated spinal cord motor neuron according to the invention exhibits one or more of the following molecular and cellular pathology as compared to a wild type (+/+) motor neuron: (a) a higher amount of TDP-43 than a wild type (+/+) motor neuron; (b) a greater amount of TDP-43 in the cytosol; (c) a reduced survival rate; and (d) a reduced axon length.

Further in another aspect, the invention relates to a method for identifying an agent alleviating and/or suppressing ALS-TDP pathogenesis, comprising: (i) applying a test agent to the isolated spinal cord motor neuron of the invention; and (ii) assaying the effect of the test agent on alleviating and/or suppressing at least one of the ALS TDP-43 associated proteinopathies and motor neuron degeneration as compared to a wild type (+/+) motor neuron; wherein alleviation and/or suppression of the at least one of the ALS-TDP pathogenesis and motor neuron degeneration as compared to the wild type (+/+) motor neuron is indicative of a candidate agent for alleviating and/or suppressing the ALS-TDP pathogenesis.

Yet in another aspect, the invention relates to a method for identifying an agent alleviating and/or suppressing ALS-TDP pathogenesis, comprising: (i) administering a test agent to the genetically modified mouse of the invention; and (ii) assaying the effect of the test agent on at least one of the ALS-TDP pathogenesis; wherein alleviation and/or suppression of the at least one of the ALS-TDP pathogenesis as compared to a control is indicative of a candidate agent for alleviating and/or suppressing the ALS-TDP pathogenesis.

In one embodiment, the ALS-TDP pathogenesis is at least one selected from the group consisting of the following ALS-like phenotypes: (a) motor dysfunction; (b) abnormal hind limb-clasping; (c) kyphosis; (d) a shorter life span than a wild type mouse; and (e) a weight loss.

In another embodiment, the ALS-TDP pathogenesis is at least one selected from the group consisting of the following molecular and cellular pathology as compared to a wild type (+/+) mouse: (a) an increased expression of TDP-43 protein; (b) an enhanced cleavage of TDP-43; and (c) an increased fraction of insoluble TDP-43/TDP-35/TDP-25; (d) mislocalization of TDP-43 from nuclei to cytoplasm of spinal cord motor neurons; (e) accumulation of ubiquitinated TDP-43 proteins in spinal cord motor neurons; and (f) a loss of spinal cord motor neurons.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1A shows Age-dependent ALS-like phenotypes of heterozygous male N390D/+ mice. A Schematic diagram of targeted knock-in (KIN) of ALS-associated mutant TDP-43, A315T and N390D (star), respectively in mouse Tardbp gene. Both sides of the NEO cassette in the targeted allele (Tardbp$^{NEO}$) was flanked by lox P sequence (grey arrowhead). The genotypes of mice carrying the different knock-in allele (Tardbp$^{KIN}$) were validated by PCR, as exemplified for two heterozygous lines each for N390D and A315T. #125 plus #180 and #108 plus #361 are the name of mouse lines of A315T and N390D, respectively.

FIGS. 1B-(a) to 1B-(b) show (a) Rotarod test of heterozygous knock-in mouse lines in comparison to the +/+ male mice. Note that both lines of N390D/+ male mice (left panel) exhibited motor dysfunction at the age of 6 months, but not the two A315T/+ mouse lines (right panel). The average time periods of mice staying on the rotarod (mean±SEM) at different ages are shown and compared in the line graphs. The numbers (N) of mice analyzed per group are listed in the figure. *p<0.05; **p<0.01, n.s., not significant. (b) Hind-limb clasping test. Exemplified are the abnormal clasping behavior of 8-month old N390D/+ male mice (right 2 panels) in comparison to their +/+ littermates (left 2 panels).

FIG. 1C shows ALS-like kyphosis phenotype of N390D/+ male mice (right panels) in comparison to the +/+ littermates (left panels) at the ages of 8 months and 18 months, respectively.

FIGS. 1D-(a) to 1D-(b) show comparison analysis of the average body weight. (a) N390D/+ male mice (left panel) as well as A315T/+ plus A315T/A315T male mice (right panel) were measured at different ages and compared to the +/+ male mice. (b) The left panel shows the comparison of the weight of remains between +/+ and N390D/+ male mice in a manner consistent with the survival curve. The right panel shows the body weight of the remains of N390D/+ male mice compared to the body weight recorded when they are still alive. Mean±SEM. The number of mice analyzed per group are listed in the figure. * p<0.05.

FIGS. 2A-(a) to 2A-(b) show patho-signature analysis of TDP-43 in spinal cord of heterozygous N390D/+ knock-in male mice. Western blotting of TDP-43 in different tissues of 6-month old A315 T/+ male mice (a) and N390D/+ male mice (b), respectively. Statistical analysis is shown in the box plots (min to max with all points). Note the elevation of TDP-43 in the spinal cord of N390D/+ male mice. Tubulin is the internal control. N=6 (3 mice from each of the two independent lines) per group. *p<0.05.

FIGS. 2B-(a) to 2B-(d) show Western blotting of soluble and insoluble fractions prepared from the spinal cord of +/+ or N390D/+ male mice at different ages using antibody against total TDP-43 (a, including TDP-35 and TDP-25). N=6 (3 mice from each of the two independent lines) per group. The statistical results are shown in (b-d). (b) The relative fold of spinal cord TDP-43 (soluble plus insoluble forms) of +/+ and N390D/+ male mice at different ages is exemplified in the upper box plots (min to max with all points). (c) The stacked bar plot (mean±SD) in the middle indicates the proportions of soluble and insoluble TDP-43, respectively, in the spinal cord of +/+ and N390D/+ male mice at different ages. (d) The connecting-line plot deduced from FIG. 2B(a) presents the changes of the fractions (%) of the soluble and insoluble TDP-43 in the spinal cord of N390D/+ and +/+ male mice, respectively. Mean±SD and *p<0.05, **p<0.01.

FIGS. 2C-(a) to 2C-(d) show immunofluorescence co-staining of spinal cord lumbar sections from +/+ and N390D/+ male mice of different ages using anti-TDP-43 (green), anti-ubiquitin (Ub, gray) and anti-ChAT (red; a motor neuron marker). The anti-ChAT staining patterns of the spinal cord MN are similar to those reported before. DAPI (blue) indicates the locations of the nuclei. The white line boxes in the first column indicate the magnified regions of panels on the right. The statistical comparison exemplified in the scatter dot plot with SD are the ChAT (+) motor neuron numbers per lumbar section (b), the % of ubiquitin (+) MN among the ChAT (+) MN (c), and the % of ChAT (+) MN with large ubiquitin (+) TDP-43 (+) MN aggregates (d). Note that: (i) mislocalization of TDP-43 from nucleus into the cytosol of spinal cord MN of 6- and 24-month old N390D/+ male mice; (ii) increase of the Ub signal in the N390D/+ spinal cord MN after the age of 6 months; (iii) appearance of TDP-43 aggregates with ubiquitin in the MN of old N390D/+ mice. At least 2 discontinuous sections of lumbar spinal cord were counted for each mouse. The scale bars are 50 µm. N≥3 (randomly chosen from each of the two independent lines) per group. *$p<0.05$, **$p<0.01$, #$p<0.001$.

FIG. 2D shows Western blotting analysis of the cytosolic and nuclear distribution of spinal cord TDP-43, TDP-35 and TDP-25 of N390D/+ and +/+ male mice at different ages. The distribution patterns of histone H4 (nuclear marker) and α-tubulin (cytosolic marker) were used to validate the fractionation of cellular extracts. The scatter plot (mean±SD) deduced from the Western blotting data are shown below the blots. N=6 (3 mice from each of the two independent lines) per group. *$p<0.05$, #$p<0.001$.

FIG. 3A shows effects of TDP-43 (N390D) mutation on autophagy. Western blotting analysis of LC3-I and LC3-II in the spinal cord of +/+, A315T/+ and N390D/+ male mice at the age of 3 and 6 months. A blotting pattern is exemplified on the top, and the statistical analysis is shown in the box plots (min to max with all points) in the lower panel. Note the increase and decrease of the LC3-II/LC3-1 ratio of the spinal cord extracts from 3-month and 6-month old N390D/+ mice, respectively, in comparison to +1+ or A315T/+ mice. N=6 (3 from each of the two independent lines) per group. **$p<0.01$, #$p<0.001$.

FIG. 3B shows Western blotting and statistical analysis (box plots; min to max with all points) of the level of TDP-43 protein in the spinal cord of newborn, 3-month and 12-month old male mice. **$p<0.01$.

FIGS. 3C-(a) to 3C-(d) show the expression patterns of Bcl-2-201 mRNA and Bcl-2 protein in the spinal cords of A315T/+, N390D/+ and +/+ male mice at the ages of newborn, 3 months and 12 months are exemplified (a), with the statistical analysis of the levels of Bcl-2 mRNA (c) and Bcl-2 protein (d) shown (min to max with all points). The scheme of the alternative splicing of Bcl-2 pre-mRNA to generate the Bcl-2-201 mRNA (the black lines) and Bcl-2-202 mRNA (the red lines) is shown (b). The 3 arrows (P1, P2 and P3) indicate the primers used for RT-PCR. Blue lines indicate location of the coding sequence. The boxes with different colors are the different exons. Indicated by arrows in the dashed frame are the primers (P2, P3) used for detecting the Bcl-2-201 mRNA. N=6 (3 from each of the two independent lines) per group. *$p<0.05$, #$p<0.001$.

FIG. 3D shows RT-PCR detection and statistical analysis (box plots; min to max with all points) of the changes of the relative ratio of the two Bcl-2 mRNA isoforms. Note the increase of functional Bcl-2-201 mRNA in the spinal cord of N390D/+ male mice at both pre-symptomatic (3-month) and symptomatic (6-month) stages. N=4 (2 from each of the two independent lines) per group. **$p<0.01$.

FIGS. 3E-(a) to 3E-(c) show comparison of the levels of Bcl-2 expression in transfected N2a cells. N2a cells were transfected with 4 µg of plasmid DNA expressing mouse wild-type TDP-43, TDP-43 (A315T), or TDP-43 (N390D). The levels of Bcl-2-201 mRNA (b) and Bcl-2 protein (c) were then assayed by RT-PCR (a, upper two panels) and by Western blotting (a, lower three panels), respectively. The statistical analysis of the levels of Bcl-2 mRNA and Bcl-2 protein are in the right two dot plots (mean±SD). Note the increases of Bcl-2 mRNA and Bcl-2 protein only in N2a cells overexpressing TDP-43 (N390D). * $p<0.05$, **$p<0.01$.

FIGS. 4B-(a) to 4B-(b) show comparative analysis of patho-signatures by (a) Western blotting analysis of TDP-43 in cultured ESC and ESC-derived spinal motor neurons (MN). MN was purified by GFP-based fluorescence sorting on different days in culture and analyzed by Western blotting with anti-TDP-43 and anti-tubulin. The statistical analysis is shown in the lower two box plots (min to max with all points). Note the drastically higher level of TDP-43 in (N390D/+) MN than (A315T/+) MN or (+1+) MN. **$p<0.01$. (b) The stability of TDP-43 polypeptides in spinal cord (N390D/+) MN, (A315T/+) MN, and (+/+) MN on day 2 in culture by cycloheximide (CHX) assay and Western blotting analysis. The graph below the blots shows that TDP-43 is more stable in (N390D/+) MN in comparison to either (+/+) MN or to (A315T/+) MN. *$p<0.05$.

FIG. 4C shows survival curves of MN in culture. The percentage(s) of GFP (+) cells in the cell mixtures on day 1 of MN culture is defined as 1. The data showed that (N390D/+) MN became more vulnerable to death than (A315T/+) MN or (+/+) MN on day 14 in culture. Mean±SD *$p<0.05$.

FIGS. 4D-(a) to 4D-(b) show neurodegeneration of cultured spinal cord MN derived from +/+ and mutant ESC by immunofluorescence co-staining analysis of MN on day 7 and day 14 in culture (a) using anti-ChAT (green or red) and anti-TDP-43 (red or white). The white boxes mark the areas magnified for higher resolution. The axonal morphology under lower magnified field is displayed with Z-axis projection. The scale bars are 50 nm. The statistical analysis of the axon lengths from the WT and mutant MN on different days in culture is shown in the line graph (b). N>50. *$p<0.05$.

FIGS. 5A-(a) to 5A-(b) show mis-regulation of Bcl-2 expression in cultured (N390D/+) MN. A. (a). Comparison of the levels of TDP-43 at early stages of ESC-derived MN in culture (from day 1 to day 3), as analyzed by Western blotting. The statistical analysis is shown in the lower scatter plot (mean±SD). * $p<0.05$. (b) Comparison of the expression levels of Bcl-2-201mRNA and Bcl-2 protein as analyzed by RT-PCR (exemplified in the upper panels) and Western blotting (exemplified in the middle panels), respectively. The statistical analysis is shown in the lower scatter plots (mean±SD). * $p<0.05$, ** $p<0.01$, # $p<0.001$. Note the elevation of Bcl-2-201 mRNA and Bcl-2 protein in MN on day 2 and day 3 in culture.

FIGS. 5B-(a) to 5B-(b) show comparison of the levels of Bcl-2 protein by Bcl-2 mRNA by RT-PCR (a) and Western blotting (b) in cultured (+/+) MN and (N390D/+) MN on day 2 and day 14, respectively. * $p<0.05$, **$p<0.01$.

FIGS. 5C-(a) to 5C-(b) show the relative levels of the cytosolic calcium ion levels in cultured MN (a) and transfected HEK-293T cells (b) overexpressing human TDP-43 (wild-type; WT), TDP-43 (A315T) or TDP-43 (N390D). The relative calcium ion levels were analyzed with the use of Fura2-AM reagent and compared in the separated scatter plots (mean±SD). Note the mis-metabolism of the cytosolic calcium ion in cultured (N390D/+) MN and in HEK-293T cells overexpressing TDP-43 (N390D) in comparison to TDP-43 (WT) and TDP-43 (A315T). *p<0.05, **p<0.01. N.S., not significant.

DETAILED DESCRIPTION OF THE INVENTION

Definitions

Figure 4A:
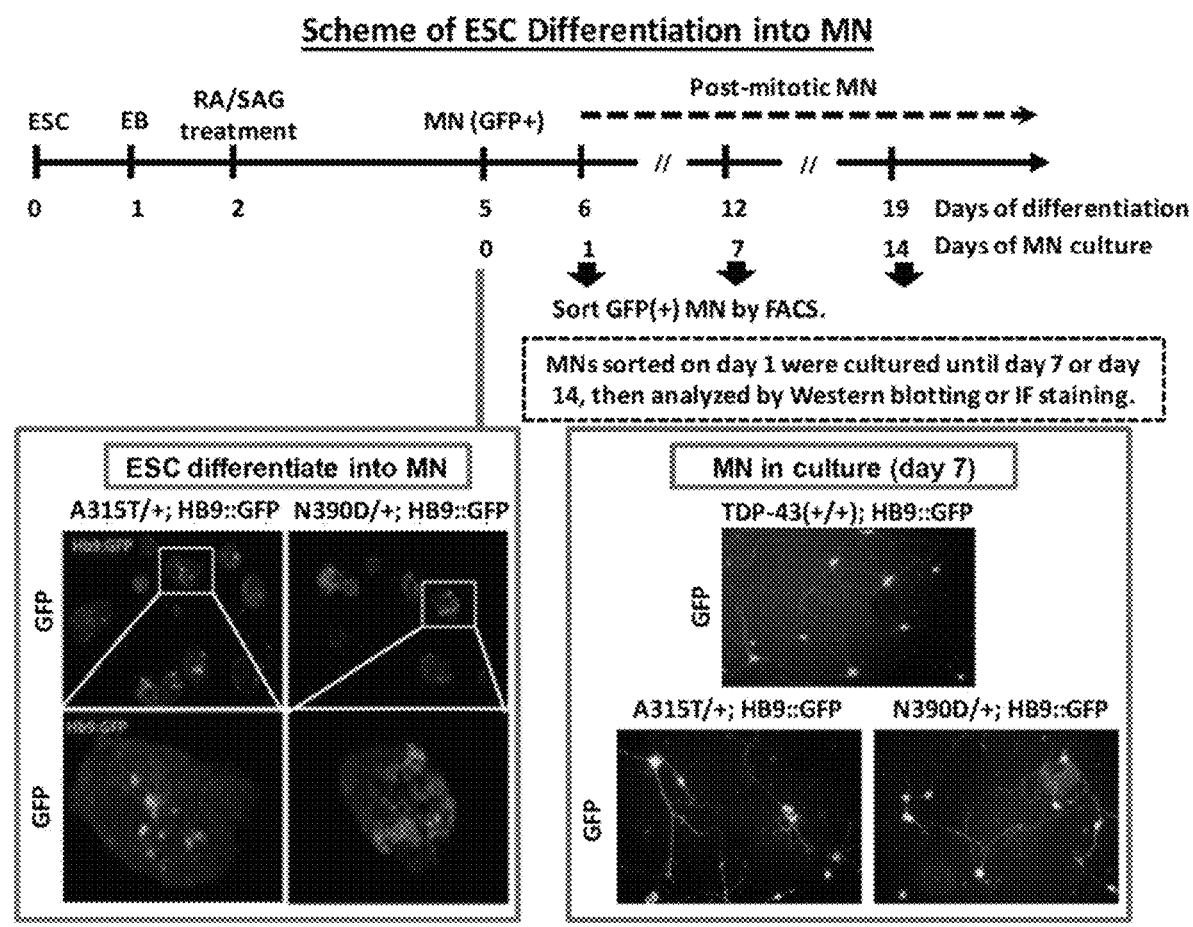
FIG. 4A shows scheme of MN differentiation (top panel). ESC from TDP-43 (+/+); Hb9:GFP, TDP-43 (A315T/+); Hb9:GFP, and TDP-43 (N390D/+); Hb9:GFP mice were differentiated into GFP(+) spinal MN (four panels in blue box) which can develop neurites in culture (three panels in red box) as described in Methods. Day 6 of the differentiation process would be day 1 of MN in culture when most (>65%) of the ESC were differentiated into GFP (+) MN (bottom right).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "a control mouse" shall generally mean a mouse whose spinal cord motor neurons do not have a loss of TDP-43 function.

The term "ALS-like symptoms" shall generally mean "symptoms associated with ALS." As used herein, "ALS-like symptoms" comprises one or more than one of the following phenotypes: a) kyphosis; b) abnormal hind limb clasping; c) deficiency in motor coordination and motor learning ability or deficiency in rotorad test; d) motor neuron loss in the spinal cord; e) astrocytosis in the spinal cord; f) weight loss compared with a control rodent; and g) accumulation of poly-ubiquitinated proteins in the spinal cord motor neurons.

The term "expressing normal amount of TDP-43" means expressing TDP-43 in an amount similar to a control mouse.

The terms "HB9" and "Hb9" are interchangeable. Expression of Hb9 protein occurs primarily in the motor neurons of the spinal cord. The Hb9 promoter is used for spinal cord motor neuron-specific transgene expression.

Cre recombinase or the Cre (causes recombination) protein consists of 4 subunits and two domains: The larger carboxyl (C-terminal) domain, and smaller amino (N-terminal) domain. The total protein has 343 amino acids. The C domain is similar in structure to the domain in the Integrase family of enzymes isolated from lambda phage. This is also the catalytic site of the enzyme.

Lox P site (locus of X-over P1) is a site on the Bacteriophage P1 consisting of 34 bp. There exists an asymmetric 8 bp sequence in between with two sets of palindromic, 13 bp sequences flanking it.

The terms "Tardbp" and "TARDBP" are interchangeable.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms refer only to the primary structure of the molecule.

Thus, the terms "gene(s)", "polynucleotide", "nucleic acid sequence", "nucleotide sequence", or "nucleic acid molecule(s)" as used herein include double- and single-stranded DNA and RNA. They also include known types of modifications, for example, methylation, "caps", substitutions of one or more of the naturally occurring nucleotides with an analog.

A "coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

*Mus musculus* TAR DNA binding protein (Tardbp), transcript variant 1, mRNA and protein sequence are SEQ ID NOs: 1 and 2, respectively. *Homo sapiens* TAR DNA binding protein (TARDBP), mRNA and protein sequence are SEQ ID NOs: 3 and 4, respectively.

Here we report the generation and characterization of two genetically modified mouse models, each bearing a single ALS-TDP associated TDP-43 knock-in mutation (N390D or A315T). Significantly, the N390D mutation, but not A315T mutation, leads to a whole spectrum of male-dominant pathological features mimicking ALS-TDP.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods

Experimental Model

Generation of TDP-43(A315T/+) and TDP-43 (N390D/+) Knock-in Mice

Standard procedures were followed to generate mouse line carrying different Tardbp (TDP-43) mutations. The targeting vector carrying mutations (A315T or N390D) on exon 6 of Tardbp was cloned in the BAC clone RP23-364M1 (Invitrogen) by using the counter-selection BAC modification kit (Gene bridges). For A315T, the nucleotide G at position 943 was substituted for A; the nucleotide A at position 1168 (of the coding sequence) was substituted for G for N390D. Mouse Tardbp nucleotide sequence is as shown in SEQ ID NO: 1, wherein 5'UTR region is nt 1 to nt 353 and coding region is nt 354 to nt 1598. The mutation position was counted from the first nucleotide of the coding sequence. A neo-resistant gene with loxP sequence cassette (PGK-neo cassette) was inserted into intron 4 of Tardbp for ES cell screening. Two independent targeted ES cell clones were expanded and microinjected into C57BL/6J (The Jackson Laboratory) blastocysts to generate the chimeric mice. Knock-in ES cells carrying A315T or N390D substitution in TDP-43 were identified by standard operating procedures of the Transgenic Core Facility of Institutional Molecular Biology, Academia Sinica. To remove the PGK-neo cassette from targeted Tardbp allele, the germline-transmitting F1 lines were crossed with EIIa-Cre mice (Tg(EIIa-cre) C5379Lmgd; The Jackson Laboratory) expressing the Cre recombinase in the whole body. The genotypes of A315T/+ or N390D/+ mice were verified by sequencing of cDNAs and genomic DNAs. All animals were maintained in a specific pathogen-free (SPF) environment under standard laboratory conditions and handled following the guidelines of the Institute Animal Care and Use Committee (IACUC) of Academia Sinica. The knock-in mice were genotyped by PCR using the forward primer 5'-GACCT-CAACTGCTCTGCTTCTACC-3' (SEQ ID NO: 5) and the reverse primer 5'-AACGGAATCAA TCCTCTCCAGG-3' (SEQ ID NO: 6).

Differentiation of Mouse ESC into Spinal Cord Motor Nearons (MN) in Culture

TDP-43 knock-in mice were crossed with B6.Cg-Tg (Hlxb9-GFP)1Tmj/J (Hb9:GFP; The Jackson Laboratory) transgenic mice to obtain offspring of the genotypes of TDP-43 (A315T+); Hb9:GFP and TDP-43 (N390D/+); Hb9: GFP, respectively. The ESCs from 3.5 day embryo were cultured and differentiated into spinal MN as depicted in FIG. 4 following the protocols described by[53,54]. Briefly, in inductive phase, ESCs were cultured in differentiation medium (45% Advanced DMEM/F12 (Gibico), 45% Neurobasal (Gibico), 10% 1 Knockout-SR (Gibico), 2 mM L-glutamine (Millipore)) to form the embryonic bodies (EBs) on day 1. On day 2, EBs were added with RA (Retinoic acid, Sigma-Aldrich) and SAG (Smoothened agonist, Cayman Chemical), a Shh pathway activator sand cultured for another 2 to 3 days to promote MN differentiation. On day 5, cells expressing GFP under the control of spinal cord motor neuron-specific promoter Hb9, i.e. MN, would appear, and the EBs were dissociated with 0.25% Trypsin-EDTA (Gibco), plated on coverslips pre-coated with 0.01% poly-D-lysine (Sigma)/0.01% omithine (Invitrogen), 5 μg/ml laminin (Invitrogen), and cultured in the MN medium (45% Advanced DMEM/FI 2, 45% Neurobasal, 10%1 Knockout-SR, 2 mM L-glutanine, 1×B27 (Gibico), 1×N2 supplement (Gibico), 10 ng/ml GDNF (Peprotech). When required, GFP (+) MNs were purified by flow-sorting in FACSAriaII SORP.

Cell Lines

Neuro 2a (N2a) cells were cultured in minimum essential medium (MEM, Gibico) supplemented with 10% FBS (Gibico), 1% sodium pyruvate (Invitrogen), 10% FBS (Gibico) and 1% antibiotics (100 IU/mL penicillin and 100 g/mL streptomycin, invitrogen), whereas HEK293T cells was cultured in Dulbecco's modified Eagle's medium (DMEM, Gibico) supplemented with 10% FBS and 1% antibiotics.

Methods

Behavior Tests

Accelerating rotarod—Mice were trained for 3 days and tested. In brief, the mice were placed on a rod (Ugo Basile Rota-Rod 47600) rotating at 4 rpm constant speed. In testing phase, the rotation speed was accelerated from 4 to 40 rpm in 5 minutes. Latency and fall-off rpm of each mouse was recorded when the mice fell from the rod.

Hindlimb-clasping test—The test was carried out. The mice were suspended by grasping their tails and their hindlimbs position were observed for 10 seconds. The normal mice consistently kept their hindlimbs away from the abdomen. Hindlimbs of the knock-in mice having motor dysfunction would be retracted toward or touching the abdomen during the suspended time.

Immunofluorescence Staining Analysis

For staining of the spinal cord, 10 μm thick sections were prepared. For staining of ESC-derived MN, the culture medium was removed, and the cells were washed gently with PBS. MN on coverslips were fixed by freshly made and pre-colded 4% paraformaldehyde for 20 min. The samples of spinal cord sections or ESC-derived MN were then permeabilized with PBS/0.5% Triton X-100 for 7 min at room temperature. After blocking with 2% fetal bovine serum (FBS) for 1 hr at room temperature, the samples were incubated overnight at 4'C with one or more of different antibodies, including goat anti-choline acetyltransferase (ChAT; Millipore), rabbit anti-TDP-43 (Proteintech), and mouse anti-Tau (Thermo Pierce), rabbit anti-ubiquitin (Proteintech), mouse anti-Hb9 (DSHB). After washing, the samples were incubated with DAPI (Invitrogen) plus Alexa-Fluor-488-conjugated secondary antibody and Alexa-Fluor-546-conjugated secondary antibody (Jackson ImmunoResearch) for 1 hr at room temperature. The images were analyzed on a Zeiss LSM 510 META confocal microscope.

Western Blotting Analysis

The mouse tissues (200 mg/ml) were extracted with RIPA buffer (0.1% SDS, 1% Nonidet P-40, 0.5% sodium deoxycholate, 5 mM EDTA, 150 mM NaCl, 50 mM Tris-HCl, pH 8.0) or urea buffer (7M urea, 2M thiourea, 4% CHAPS, 30 mM Tris-HCl, pH 8.5) containing protease and phosphatase inhibitors (Roche). After homogenization and centrifugation of the tissue at 13,000 rpm 4° C. for 30 min, the solution from the urea buffer-derived extract was defined as the "total protein extract", and the supernatant from the RIPA buffer extract(s) was defined as the "soluble fraction". The pellet from the RIPA buffer-derived extract was washed by RIPA buffer for 3 times, dissolved in urea buffer, and defined as the "insoluble fraction". The cellular extracts of cultured MN were prepared in the following way. The cultured spinal MN (see below) were purified by GFP (+)-based sorting in FACSAriaII SORP. The purified GFP (+) MNs were cultures for different days and lysed with lysis buffer. $1*10^6$ MNs were lysed with either RIPA buffer or urea buffer. The different protein extracts were separated by 12% SDS-PAGE and immunoblotted with the appropriate primary antibodies (anti-TDP-43 from Proteintech, anti-ubiquitin from Proteintech, anti-histon H4 from Millipore, anti-LC3 from NOVAS, anti-Bcl-2 from Proteintech, anti-tubulin from Sigma and anti-actin from Sigma) and then the secondary antibodies. The bound antibodies were detected by using the chemiluminescence Western blotting detection reagent ECL (Amersham Pharmacia Biotech, Piscataway, N.J.). The expression levels of different proteins were compared by measuring their band intensities on the blots with Image J software (NIH).

Preparation of Nuclear and Cytosolic Extracts

Briefly, spinal cord was lysed gently with 10× (vol./weight) hypotonic buffer A (10 mM Hepes-KOH, pH 7.4, 10 mM KCl, 1.5 mM MgCl, 0.5 mM EDTA, 0.5 mM EGTA) containing protease inhibitors (Roche) by homogenization. After 15 min on ice, 0.5% NP-40 was added and the samples were vortexed and centrifuged at 800 g for 5 min at 4° C. The supernatant was defined as the cytosolic fraction. For preparation of the nuclear extract, the nuclear pellet was washed with hypotonic buffer A, added 5× (vol/wt) extraction buffer (10 mM Hepes-KOH, pH 7.4, 0.42 M NaCl, 2.5% (vol/vol) glycerol, 1.5 mM MgCl, 0.5 mM EDTA, 0.5 mM EGTA, 1 mM DTT) containing protease inhibitors, and then incubated at 4° C. while rotating at 60 rpm for 40 min.

Survival Rate Analysis of Cultured MN

A modified MN induction protocol was used for this analysis. On day 5 of the differentiation phase, the EBs were directly cultured in the MN medium without dissociation by trypsin. The EBs were then examined by FACS (LSRII-12P) for 14 days in culture. The percentage of the GFP (+) MN in the EBs on the $1^{st}$ day was defined as 100% and the folds of change on the following days were quantitated and compared for the WT and mutant MN.

RT-PCR and RT-qPCR Analysis

Total RNAs from the tissues or cells were isolated following the standard protokol using Trizol reagent (Thermo Fisher Scientific). cDNA synthesis was carried out using SuperScript II reverse transcriptase (Invitrogen) and subjected to PCR. Alternatively, real-time PCR (qPCR) using SYBR Green PCR Master Mix (Applied Biosystems) and ABI 7500 real-time System was carried out. All data were analyzed after normalization to the expression level of the Gapdh gene. The sequences of the PCR primers are listed below:

```
Tardbp forward primer:
                                    (SEQ ID NO: 7)
5'-GGTAATCCAGGTGCTTTG-3';

Tardbp reversed primer:
                                    (SEQ ID NO: 8)
5'-CCTGCATTTGATGCTGACCC-3';

Bcl-2 splicing forward primer (P1):
                                    (SEQ ID NO: 9)
5'-TTCGGGGAAGGATGGCGCAAGC-3';

Bcl-2-201 forward primer (P2):
                                    (SEQ ID NO: 10)
5'-ACGGAGGCTGGGATGCCTTTGTGG-3';

Bcl-2 reversed primer (P3):
                                    (SEQ ID NO: 11)
5'-TCACTTGTGGCCCAGGTATGC-3'
```

Expression Plasmid Construction and DNA Transfection cDNAs of mouse wild type TDP-43, TDP-43 (A315T) and TDP-43 (N390D) with addition of a Myc epitope tag to the 3'-end were generated by RT-PCR of different mouse spinal cord RNAs as the templates. The PCR primers used were: forward 5'-CCG CTC GAG CGG ATG TCT GAA TAT ATT CGG GTA AC-3' (SEQ ID NO: 12); reverse 5'-TGC TCT AGA GCA CAT TCC CCA GCC AGA C-3' (SEQ ID NO: 13). These cDNA fragments were first cloned into pGEM-T vector (Promega Corporation) and then subcloned into the XhoI/XbaI sites of pEF-myc vector (Promega Corporation). The generation of expression plasmids carrying human wild-type TDP-43, TDP-43 (A315T), and TDP-43 (N390D) cDNA, respectively, was described in Wu et al. (2013).

DNA Transfection

The N2a cells were transfected with the pEF-myc vector or different mouse TDP-43 expression plasmids. HEK293T cells were transfected with the vector or different human TDP-43 expression plasmids. DNA transfection was carried out with Lipofectamine 2000 (Invitrogen) according to the manufacturer's protocol. The amount of the plasmid DNA used in each transfection was 4 μg per 6-cm dish. The cells were harvested at 24 hr post-transfection and analyzed by different assays, e.g. Western blotting, calcium imaging, etc.

Cyclohexamide Chase Assay

In brief, MNs on day 2 were treated with cycloheximide (20 mg/ml) for different time periods (2, 4, 8, 12 and 24 hr). The levels of TDP-43 in the treated MN were analyzed by Western blotting and the relative intensities of the TDP-43 bands were quantified by AlphaEaseFC software. The data were expressed as means±SD. Note the significantly higher stability of TDP-43 in MN (N390D/+) than that in MN (+/+) as shown in FIG. 4B-b. *p<0.05.

Calcium Imaging

MNs were dissociated on differentiation day 5, plated on coated 22×22 mm glass coverslips, and grown in MN medium until calcium imaging experiments. HEK293T cells were cultured on 0.1% gelatin-coated 22×22 mm glass coverslips and transfected with plasmid DNAs for 24 hr before calcium imaging. Before calcium imaging, the MNs were treated with 2 uM Fura-2-AM (Invitrogen) in HBSS (Invitrogen) containing 2 mM $CaCl_2$ in the dark chamber and incubated at 37° C., 5% $CO_2$ for 45 min. The excess Fura-2-AM was washed out with HBSS (without $CaCl_2$) and incubated for an additional 30 min in HBSS (containing 2 mM $CaCl_2$)) for recovering, and then the coverslips were transferred onto the recording chamber of an inverted fluorescence microscope (Zeiss Axiovert 200) equipped with a 20× objective lens and MetaFluor (Molecular Devices) acquisition and analysis software. The fluorescence signals at 510 nm were acquired every 2 seconds in 5 min by UV excitation at wavelengths of 340 nm (indicating calcium ion-bound-Fura-2-AM) and 380 nm (indicating calcium ion-free-Fura-2-AM), respectively. The formula $$R = \frac{\Delta 340}{\Delta 380},$$

in which the Δ indicated the values of 340 nm or 380 nm minus their background values, was used to calculate and compare the relative levels of intracellular calcium ion of different types of MN in culture.

Statistical Analyses

Statistical differences were analyzed by Kaplan-Meier and log rank test(s) for the survival rates, two-way ANOVA and Bonferroni post hoc analysis for multiple group comparisons, and the unpaired Student's t-test for two group comparisons (SPSS version 15.0, SPSS Inc. and Prism (version 7, GraphPad software). The error bars of mouse behavior were showed by SEM, and the error bars of molecule and cellular analysis were displayed by SD.

Results

An ALS-Like Phenotype of Mice Bearing a Single TDP-43 N390D Mutation, but not an A315T Mutation We generated mouse lines bearing homologous knock-in of human ALS-associated base substitutions, A315T and N390D, respectively. The TDP-43 A315T was identified in all affected members but not the healthy control subjects of several European families, while N390D was identified in a sporadic ALS-TDP patient from Quebec (Gitcho, M. A. et al. 2008; Kabashi, E. et al. 2008). We substituted the conserved nucleotide G at position 943 with A (for A31 ST) or A at position 1,168 with G (for N390D) in the mouse tardbp gene (FIG. 1A). Surprisingly, while heterozygous male N390D/+ mice derived from 2 independent lines exhibited motor dysfunction at the age of 6 months, heterozygous A315T/+ mice appeared indistinguishable from wild type (+/+) littermates (FIG. 1B-a). Furthermore, the N390D/+ mice started to show abnormal hind limb-clasping and kyphosis at around 8 months of age, as shown in FIG. 1B-b and FIG. 1C, respectively. N390D/+ mice also displayed spastic and trembled gait at 18 months and beyond (Movie 1 and Movie 2). Furthermore, the N390D/+ mice displayed a shorter life span than either +/+ or A315T/+ mice, with average age of 19±2 months. Finally, while +/+, A315T/+, and N390D/+ alive mice had similar body weights (FIG. 1D-a), conspicuous weight loss was observed in the remains of N390D/+ mice (FIG. 1D-b). This phenomenon was similar to the sudden loss of body weight observed in ALS patients as the result of dysfunction of all muscles under voluntary control (Wills, A. M. et al (2014)). Notably, the disease-onset ages of individual female N390D/+ mice were highly variable, with the average being 12 months, which was later than the male N390D/+ mice. Furthermore, 30% of female mice were indistinguishable from the +/+ mice (data not shown).

Molecular and Cellular Pathology of the TDP-43 (N390D/+) Mice

Accumulation, Enhanced Cleavage. And Increased Insolubility of Spinal Cord TDP-43, Changes in a range of molecular and cellular characteristics were associated with the ALS-like phenotypes of the male N390D/+ mice described above. First, in contrast to A315T/+ mice, the expression level of TDP-43 protein was progressively elevated with age in the spinal cord, but not in other tissues, of male N390D/+ mice, at the post-symptomatic ages, e.g. 6, 12 and 24 months (FIG. 2A and FIG. 2B-b) as well as at pre-symptomatic ages, e.g. 3 months (FIG. 2B-b), despite the similar levels of tardbp mRNA. Second, there was an age-dependent enhancement of cleavage of TDP-43 to generate 35-kDa and 25-kDa C-terminal fragments in the spinal cord of post-symptomatic N390D/+ mice (FIGS. 2B-a and 2B-b), which was characteristic of the spinal cord of ALS-TDP patients (Neumann, M. et al. 2007; Scotter, E. L. et al. 2015). The enhanced cleavage of TDP-43 was accompanied by significantly increased fraction of insoluble TDP-43/TDP-35/TDP-25 in the spinal cord extracts from N390D/+ male mice at the age of 6 months and beyond (FIGS. 2B-a, 2B-c and 2B-d).

Age-Dependent Mislocalization of TDP-43 in Spinal Cord MNs, Accumulation of Ubiquitinated Proteins in Spinal Cord MNs. And Spinal Cord MNs Loss A characteristic of ALS pathogenesis is the formation of large cytosolic TDP-43 (+), ubiquitin (+) aggregates, and depletion of nuclear TDP-43 in diseased motor neurons (Neumann, M. et al. 2006). The pathogenic significance of these aggregates with regard to the initiation and/or progression of the diseases is not well understood. As shown in FIGS. 2C-a and 2C-d, a portion of the nuclear TDP-43 in the spinal cord MNs of 6-month-old N390D/+ mice, but not the 3-month-old mice, formed punctate aggregates in the cytoplasm (diameter >2 μm). The percentage of cytosolic TDP-43 of spinal cord MNs was ~15% in 6-month-old N390D/+ mice and increased to ~40% by 24 months, as shown by Western blotting of fractionated cell extracts (FIG. 2D). The age-dependent mislocalization of TDP-43 in spinal cord MNs of TDP-43 (N390D/+) mice was comparable to an increase of the level of ubiquitinated proteins, as shown by immunofluorescence staining of spinal cord MNs using anti-ChAT and anti-ubiquitin antibodies (FIGS. 2C-a and 2C-c). These changes were accompanied by progressive spinal cord MNs loss after the age of 6 months and beyond (FIGS. 2C-a and 2C-b).

Alterations of Autophagy

These data clearly revealed abnormal TDP-43 intracellular localization and aggregation in the spinal cord of the N390D/+ mice in concert with the misregulation of TDP-43 metabolism. The occurrence of TDP-43 protein aggregate is known to be countered by the combined actions of the ubiquitin proteasome system (UPS) and macroautophagy, including chaperone-mediated autophagy (CMA). We therefore analyzed the relative amounts of the critical autophagy proteins LC3-I and LC3-II present in cellular extracts from mouse spinal cords. As shown in FIG. 3A, while the ratio of LC3-I/LC3-1 in the spinal cord of 3-month-old N390D/+ mice was higher than that of A315T/+ or +/+ mice, it decreased during the post-symptomatic stage to a level significantly lower than that observed in the 6-month-old A31 ST/+ and +/+ mice. This data clearly revealed the presence of TDP-43 dependent pathology of the autophagy system in the spinal cord of symptomatic N390D/+ mice.

Increase of Spinal Cord Bcl-2 Protein as a Consequence of Mis-Regulation of Bcl-2 Pre-mRNA Splicing in N390D/+ Mice Among the regulators of the autophagy pathway and neuron survival is the Bcl-2/Beclin-1 complex. Significantly, while there was no difference between the levels of spinal cord Bcl-2 protein among the newborn of +/+, A315T/+ and N390D/+ mice, the amount of spinal Bcl-2 of N390D/+ mice was higher than that of the +/+ or A315T/+ mice by approximately 1.5, 2, and 4-fold at the ages of 3, 6, and 12 months, respectively, in parallel to the increase of the spinal TDP-43 protein (FIG. 3B).

Bcl-2 mRNA is one of the potential neuronal RNA targets of TDP-43, thus, we suspected that the higher levels of Bcl-2 protein in the N390D/+ spinal cord might be at least in part due to misregulation of Bcl-2 pre-mRNA splicing. Mouse Bcl-2 mRNA consists of 2 splicing variants, Bcl-2-201 and Bcl-2-202 (Ensembl), the former of which encodes the well-studied Bcl-2 protein (NP_033871 from NCBI). Indeed, there was an excellent correlation between the age-dependent increase of spinal Bcl-2 protein and that of the functional Bcl-2 mRNA, i.e. the isoform 201 in the N390D/+ mice, as shown by RT-PCR analysis (FIG. 3C-a). The ratio of the 2 Bcl-2 mRNA isoforms was quantitated using primer 1 and primer 3 in RT-PCR analysis (FIG. 3D). Significantly, the data of FIG. 3C and FIG. 3D suggested that the increase of Bcl-2 mRNA 201 resulted from misregulation of Bcl-2 alternative pre-mRNA splicing in the spinal cord of N390D/+ mice.

To investigate the possibility that the increase of TDP-43 (N390D) plays a causative role in altering the alternative splicing of Bcl-2 pre-mRNA towards the generation of higher level of Bcl-2-201 mRNA, we carried out DNA transfection analysis in mouse Neuro-2a (N2a) cell culture (FIG. 3E). As seen, under the condition of equal amounts of exogenously overexpressed mouse wild-type TDP-43, TDP-43 (A315T) and TDP-43 (N390D), respectively, the endogenous Bcl-2 mRNA 201 (FIGS. 3E-a and 3E-b) and Bcl-2 protein (FIGS. 3E-a and 3E-c) were elevated only in N2a cells containing the exogenous TDP-43 (N390D). Taken together, the data of FIG. 3 demonstrate that at comparable high levels, only mutant TDP-43 (N390D), but not wild-type or mutant TDP-43 (A315T), increases the expression of Bcl-2 mRNA isoform 201 as the result of changes in alternative splicing of the Bcl-2 pre-mRNA.

TDP-43 Proteinopathies and MN Degeneration in Culture

To examine whether the differential effects of TDP-43 (N390D and A315T) knock-ins on ALS pathogenesis were due, at least in part, to cell-autonomous effects on spinal cord motor neurons (MNs), we generated spinal cord MNs in culture. To accomplish this, the N390D/+ and A3151/+ mice were crossed with Hb9:GFP transgenic mice. Embryonic stem cells (ESCs) were derived from TDP-43 (A315T/+)/Hb9:GFP or TDP-43 (N390D/+)/Hb9:GFP mice, and then differentiated in culture to generate MNs (FIG. 4A). As shown by Western blotting, in contrast to wild type ESC-generated motor neurons, the level of TDP-43 in ESC-derived mutant (A315T/+) MNs was 2- to 4-fold higher than the (+/+) MNs on day 7 and day 14, respectively, in culture. On the other hand, the level of TDP-43 in mutant (N390D/+) MNs was 6- and 11-fold higher than (+/+) MNs on culture day 7 and day 14, respectively, with the appearance of TDP-35 species on day 14 in culture (FIG. 4B-a). The higher amount of TDP-43 in MNs could be in part due to increased stability of the mutant TDP-43 proteins (FIG. 4B-b).

Despite of the higher levels of TDP-43, the survival curves as well as the average axonal lengths of the mutant MNs were similar to those of (+1+) MNs up to 7 days in culture (FIGS. 4C and 4D). However, on day 14 in culture, the survival (FIG. 4C) and average axon length (FIG. 4D) of (N390D/+) MNs was significantly reduced in comparison to (+/+) MNs or (A315T/+) MNs. Similar to (+/+) MNs, the majority of TDP-43 of the mutant MNs was confined in the nucleus prior to 7 days in culture, as shown by immunofluorescence staining (upper panels of FIG. 4D-a). However, the amount of TDP-43 was greater in the cytosol of (N390D/+) MNs on day 14 in culture, but without TDP-43 aggregate formation, as shown in the lower panels of FIG. 4D-a. This observation was similar to that of the post-symptomatic spinal cord MNs of N390D/+ mice (FIG. 2C-a). Thus, the analysis of cultured MNs derived from ESC suggests that time-dependent, spinal cord MN-autonomous toxic effects underlie the role of the N390D mutation of TDP-43 in age-dependent ALS-like pathogenesis of N390D/+ mice.

Increase of Bcl-2 mRNA and Bcl-2 Protein in Cultured (N390D/+) MN

Significantly, in parallel to the time-dependent increase of the TDP-43 level (FIG. 5A-a), there was an increase of either Bcl-2 mRNA 201 or Bcl-2 protein (FIGS. 5A-b and 5B). On the other hand, the levels of Bcl-2 mRNA 201 and Bcl-2 protein in (A315T/+) MNs were similar to those of(+/+) MNs on culture day 1-3 (FIG. 5A-b) and 14 (data not shown), despite of the increase of TDP-43 in cultured (A315T/+) MNs (FIG. 5A-a and data not shown). The data of FIGS. 3 and 5 together indicate that there are cell-autonomous mis-regulation of Bcl-2 pre-mRNA splicing and consequent increase of Bcl-2 protein in (N390D/+) MNs as caused by the increased level of TDP-43. Furthermore, there is a lag between the time on-set of Bcl-2 protein increase and MN degeneration.

Changes of Calcium Ion Homeostasis in Cultured (N390D/+) MN

Since Bcl-2 is known to increase ER calcium ion leakage resulting in overloading of the cytosolic calcium ion ($Ca^{2+}$), we examined the intracellular level of calcium ion in ESC and ESC-derived spinal MN. As seen, the cytosolic calcium ion concentrations in the (N390D/+) ESC-derived MN was higher than those derived from (+/+) ESC or (A315T/+) ESC (FIG. 5C-a), despite similar concentration of calcium ion in (+/+) ESC, (A315T/+) ESC and (N390D/+) ESC (data not shown). Furthermore, overexpression of human TDP-43 (N390D) provoked the intracellular level of calcium ion in HEK293T cells, but not in those cells overexpressing similar amount of either wild-type TDP-43 or TDP-43 (A315T) (FIG. 5C-b). The above data taken together show that elevation of the cellular level of TDP-43 (N390D) indeed would increase the intracellular cytosolic calcium ion concentration as a result of the increase of Bcl-2 protein.

Discussion

The availability of appropriate ALS mouse models is essential for understanding ALS disease mechanisms and the development of therapeutic drugs. Most of previously developed ALS-TDP mouse models are based on a transgenic approach, whereby wild type or mutant TDP-43 is expressed under the control of different promoters (Liu, Y. C. et al. 2013; D'Alton, S. et al. 2014; Ditsworth, D. et al. 2017; Tsai, K. J. et al. 2010). This approach is limited by the cell type specificity of the promoters used to express the wild type and mutant TDP-43 transgenes, so the timing and level of the transgene expression is difficult to control. Furthermore, transgene over-expression causes neurotoxicity and other side effects due to the differences in the timing and level of the transgene expression, even with the wild type TDP-43 gene. Here we describe the use of knock-in strategy to study ALS pathogenesis as a consequence of different ALS-associated TDP-43 mutations. A comparative analysis of the two heterozygous mouse models, N390D/+ and A315T/+, and their ESC-derived spinal cord MNs clearly demonstrate the distinctive pathological effects of different TDP-43 mutants.

It is somewhat unexpected but not totally surprising that in the genetic background of C57BL/6J mice, only N390D but not A315T mutation of TDP-43 exhibits a dominant causative role in ALS-TDP pathogenesis (FIG. 1). A315T is an extensively studied fALS mutation. Analysis of transgenic rodent models or transfected cell cultures have suggested that overexpression of human TDP-43$^{A315T}$ causes neuron degeneration and dosage-dependent cytotoxicity, induces ER stress, and affects neuronal mitochondrial morphology. Noteworthy, mice expressing human TDP-43$^{A315T}$ under the control of endogenous mouse Tarabp promoter develop mitochondria dysfunction but without obvious ALS-like pathological phenotypes. Thus, the A315T substitution in either mouse TDP-43 or human TDP-43 appears to be insufficient to cause ALS pathogenesis under certain genetic backgrounds. It has been proposed that one or more environmental stresses may play important roles in the initiation and/or progression of ALS pathogenesis. The non-symptomatic A315T/+ mice and the subtle-phenotype Q331K mice may be suitable models for future study of the interplay between the genetic and environmental factors in pathogenesis of ALS-TDP and FTD-TDP.

In striking contrast, we find that the N390D/+ mice develop molecular, cellular, and behavioral changes, with a spectrum of ALS-like phenotypes that appear at the age the 6 months and then progress (FIG. 6), These phenotypes include age-dependent motor dysfunction (FIG. 1B-a), kyphosis (FIG. 1C), weight loss (FIG. 1D-b), and shortened lifespan. These phenotypes are accompanied by various molecular and cellular pathologies (FIG. 6) including the progressive increase of TDP-43/TDP-35/TDP-25 (FIG. 2), insoluble TDP-43 species (FIG. 2B-a), and highly ubiquithiated proteins in the spinal cord (FIGS. 2C-a and 2C-d), as well as accumulation of TDP-43 protein in the cytosol of spinal cord MN of symptomatic N390D/+ mice (FIGS. 2C and 2D). Notably, there is also a progressive change of autophagy in the spinal cord of N390D/+ mice, as reflected by changes in the LC3-II/LC3-I ratio (FIG. 3A). The ratio observed in pre-symptomatic (3-month-old) N390D/+ mice was higher than that of the wild-type mice (FIG. 3A), which we speculate to be due to the autophagy response to TDP-43 aggregation, e.g. the stabilization of ATG-7 mRNA by elevated levels of TDP-43. The decreased autophagy function in the spinal cord of 6-month-old N390D/+ mice, as reflected by the decreased ratio of LC3-II/LC3-I (FIG. 3A), could be part of the molecular basis of disease progression in the spinal cord (FIG. 2).

Of particular interest and importance is the finding of the concomitant increase of the levels of TDP-43 and the Bcl-2 mRNA 201 encoding the 26 kDa Bcl-2 protein in the spinal cord of 3-month and 6-month-old, but not the newborn, N390D/+ mice (FIG. 3B) as well as in cultured spinal cord (N390D/+) MNs at differentiation day 2 and beyond (FIG. 5A-b). Bcl-2 is an anti-apoptotic protein that promotes the survival of neurons and other types of cells. Bcl-2 protein is also known to affect autophagy, intracellular calcium ion homeostasis, and consequently the associated cell-fate determining pathways in a dose-dependent manner.

Figure 6:
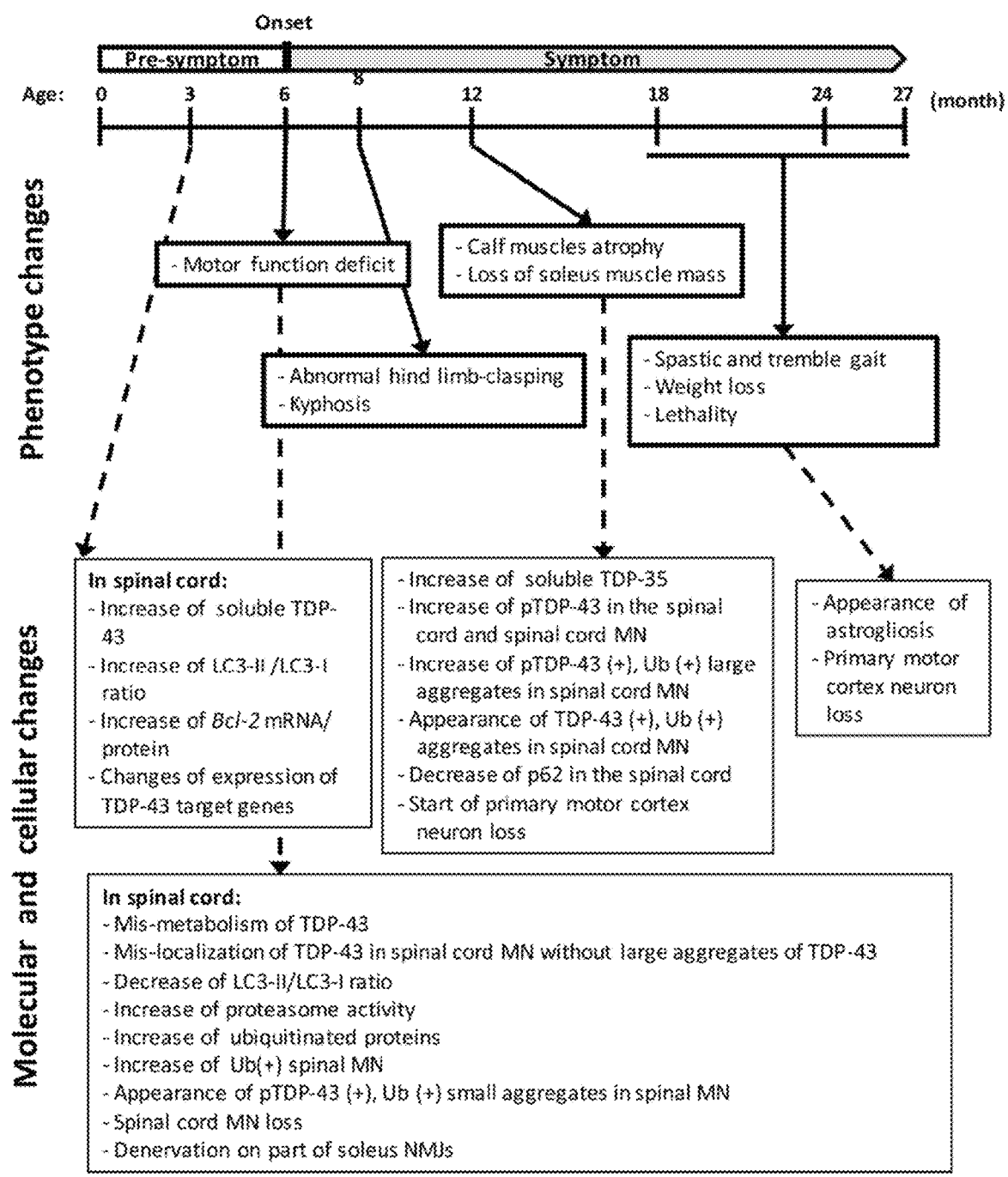
FIG. 6 shows age-dependent ALS-TDP-like pathogenesis of TDP-43 (N390D/+) male mice. The timeline (month) illustrates the major morphological, behavioral, cellular, and molecular events during the pre-symptomatic and symptomatic stages of heterozygous male TDP-43 (N390D/+) mice.

Overall, our data indicate that spinal cord-specific increase of TDP-43 (N390D), due in part to its higher stability (FIG. 4B-b), is one of the essential early causative events of ALS pathogenesis of the TDP-43 (N390D/+) mice (FIG. 6). This leads to progressive changes of autophagy (FIG. 3A), ER stress as reflected by the increases of cytosolic calcium ion in cultured spinal cord (N390D/+) MNs (FIG. 5C), enhanced cleavage of TDP-43 to generate TDP-35 and TDP-25 fragments (FIG. 2B) and facilitating the formation of cytosolic TDP-43 (+), ubiquitin (+) aggregates (FIG. 2C), all of which would contribute to the age-dependent cytotoxicity/death of the spinal cord MNs and other age-dependent ALS-like phenotypes (FIG. 1) of the TDP-43 (N390D/+) mice.

In summary, the establishment and comparative analysis of the two mouse models, TDP-43 (N390D/+) and TDP-43 (A315T/+), suggest that different human ALS-associated TDP-43 mutations display distinct pathophysiological changes in mice. In particular, the N390D mutation appears to cause alternative splicing-mediated elevation of Bcl-2 protein and thus display a toxic gain-of-function of TDP-43 (N390D). The TDP-43 (N390D/+) mice should provide an excellent model to study in detail the initiation and propagation of ALS-TDP under normal physiological conditions.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

REFERENCES

D'Alton, S. et al. Divergent phenotypes in mutant TDP-43 transgenic mice highlight potential confounds in TDP-43 transgenic modeling. *PloS one* 9, e86513, doi:10.1371/journal.pone.0086513 (2014).

Ditsworth, D. et al. Mutant TDP-43 within motor neurons drives disease onset but not progression in amyotrophic lateral sclerosis. *Acta Neuropathol* 133, 907-922, doi: 10.1007/s00401-017-1698-6 (2017).

Gitcho, M. A. et al. TDP-43 A315T mutation in familial motor neuron disease. *Annals of neurology* 63, 535-538, doi:10.1002/ana.21344 (2008).

Kabashi, E. et al. TARDBP mutations in individuals with sporadic and familial amyotrophic lateral sclerosis. *Nature genetics* 40, 572-574, doi:10.1038/ng.132 (2008).

Liu, Y. C., Chiang, P. M. & Tsai, K. J. Disease animal models of TDP-43 proteinopathy and their pre-clinical applications. *International journal of molecular sciences* 14, 20079-20111, doi:10.3390/ijms141020079 (2013).

Neumann, M. et al. Ubiquitinated TDP-43 in frontotemporal lobar degeneration and amyotrophic lateral sclerosis. *Science* 314, 130-133, doi:10.1126/science.1134108 (2006).

Neumann, M. et al. TDP-43-positive white matter pathology in frontotemporal lobar degeneration with ubiquitin-positive inclusions. *Journal of neuropathology and experimental neurology* 66, 177-183, doi:10.1097/01.jnen.0000248554.45456.58 (2007).

Scotter, E. L., Chen, H. J. & Shaw, C. E. Erratum to: TDP-43 Proteinopathy and ALS: Insights into Disease Mechanisms and Therapeutic Targets. *Neurotherapeutics: the journal of the American Society for Experimental Neuro-Therapeutics* 12, 515-518, doi:10.1007/s13311-015-0351-0 (2015).

Tsai, K. J. et al. Elevated expression of TDP-43 in the forebrain of mice is sufficient to cause neurological and pathological phenotypes mimicking FTLD-U. *The Journal of experimental medicine* 207, 1661-1673, doi: 10.1084/jem.20092164 (2010).

White, M. A. et al. TDP-43 gains function due to perturbed autoregulation in a Tardbp knock-in mouse model of ALS-FTD. *Nature neuroscience* 21, 552-563, doi: 10.1038/s41593-018-0113-5 (2018).

Wills, A. M. et al. Hypercaloric enteral nutrition in patients with amyotrophic lateral sclerosis: a randomised, double-blind, placebo-controlled phase 2 trial. *Lancet* 383, 2065-2072, doi:10.1016/S0140-6736(14)60222-1 (2014).

What is claimed is:

1. A TDP-43 knock-in mouse model of amyotrophic lateral sclerosis (ALS) whose genome comprises a heterozygous mutation encoding an N390D substitution in the Tardbp (TDP-43) gene, wherein the expression of the TDP-43 protein is elevated in the spinal cord but not in other tissues of the mouse as compared to a wild-type (+/+) mouse, wherein the mouse exhibits ALS-like phenotypes, TDP-43 proteinopathies, and/or motor neuron degeneration.

2. The TDP-43 knock-in mouse of claim 1, wherein the ALS-like phenotypes comprise kyphosis.

3. The TDP-43 knock-in mouse of claim 1, wherein the mouse is male.

4. The TDP-43 knock-in mouse of claim 1, wherein the ALS-like phenotypes comprise motor dysfunction.

5. The TDP-43 knock-in mouse of claim 1, wherein the ALS-like phenotypes comprise one or more of the following phenotypes:
   (a) motor dysfunction,
   (b) abnormal hind limb-clasping,
   (c) kyphosis,
   (d) shorter life span than the wild type, and
   (e) weight loss.

6. A body part isolated from the TDP-43 knock-in mouse of claim 1.

7. The body part of claim 6, which is selected from the group consisting of a cell, a tissue, and an organ.

8. The TDP-43 knock-in mouse of claim 1, wherein the substitution is at nucleotide A of position 1168 of the TDP-43 coding sequence.

9. The mouse of claim 8, wherein the nucleotide A at position 1168 of the TDP-43 gene coding sequence is substituted with the nucleotide G.

10. The TDP-43 knock-in mouse of claim 1, whose spinal cord exhibits one or more of the following molecular and cellular pathology as compared to the wild type:
    (a) an increased total TDP-43 protein at pre-symptomatic and post-symptomatic ages and progressively elevated with age,
    (b) an enhanced cleavage of TDP-43,
    (c) an increased fraction of insoluble TDP-43/TDP-34/TDP-28,
    (d) mislocalization of TDP-43 from nuclei to cytoplasm of spinal cord motor neurons,
    (e) accumulation of ubiquitinated TDP-43 proteins in spinal cord motor neurons, and
    (f) a loss of spinal cord motor neurons.

11. An embryo that is an offspring of the mouse of claim 1, wherein the embryo is heterozygous for the mutation.

12. An embryonic stem cell (ESC) isolated from the embryo of claim 11.

13. An isolated spinal cord motor neuron that is differentiated from the ESC of claim 12.

14. The isolated spinal cord motor neuron of claim 13, which exhibits a higher amount of TDP-43 than a wild-type (+/+) spinal cord motor neuron.

15. The isolated spinal cord motor neuron of claim 13, which exhibits one or more of the following molecular and cellular pathobgy as compared to a wild-type (+/+) motor neuron:
    (a) a higher amount of TDP-43,
    (b) a greater amount of TDP-43 in the cytosol,
    (c) a reduced survival rate, and
    (d) a reduced axon length.

16. The embryo of claim 11, wherein the embryo is an offspring resulting from a cross between the TDP-43 knock-in mouse of claim 1 and a genetically modified mouse whose genome comprises an Hb9:GFP transgene.

17. An ESC isolated from the embryo of claim 16.

18. An isolated spinal cord motor neuron differentiated from the ESC of claim 17.

19. A method for identifying a candidate agent for alleviating and/or suppressing ALS-TDP pathogenesis, comprising:
    (a) applying a test agent to the isolated spinal cord motor neuron of claim 15, and
    (b) assaying the effect of the test agent on alleviating and/or suppressing at least one of the TDP-43 proteinopathies and motor neuron degeneration as compared to a wild-type (+/+) motor neuron,
    wherein alleviation and/or suppression of the at least one of the TDP-43 proteinopathies and motor neuron degeneration as compared to the wild type (+/+) motor neuron is indicative of a candidate agent for alleviating and/or suppressing the ALS-TDP pathogenesis.

20. A method for identifying a candidate agent for alleviating and/or suppressing ALS-TDP pathogenesis, comprising:
    (a) administering a test agent to the TDP-43 knock-in mouse of claim 1 and
    (b) assaying the effect of the test agent on at least one of the ALS-like phenotypes,
    wherein alleviation and/or suppression of the at least one of the ALS-like phenotypes as compared to a control is indicative of a candidate agent for alleviating and/or suppressing ALS-TDP pathogenesis.

* * * * *

```
                        SEQUENCE LISTING

<160> NUMBER OF SEQ ID NOS: 13

<210> SEQ ID NO 1
<211> LENGTH: 7477
<212> TYPE: DNA
<213> ORGANISM: Mus musculus

<400> SEQUENCE: 1
atctaccgcg ttacgtaggg ggactcggaa ggccgagtgg ccgttctgtc cttcatctgt      60 cagttttttca gacccagctg ttttcattgt tgcgtttctt tactttttttc tatacgccga    120 agagcctgct agcatccgag cctctgggag gagagagcgc ctgtggcttc cctcggagag     180
cgcccctcct gcagggaagc cagtgggaga ggccgaaggc gggcgagggc gggaggcggc     240
cctagcgcca ttttgtgggc acggagcggt agcgcggctg ttgtcggatt ccttcccgtc     300
tgtgcttcct ccttgtgctt cctagcagtg gcctagcgga gatttaagca aagatgtctg     360
aatatattcg ggtaacagaa gatgagaacg atgaacccat tgaaatacca tcagaagacg     420
atgggacggt gttgctgtcc acagttacag cccagtttcc aggggcatgc ggcctgcgct     480
accggaatcc cgtgtctcag tgtatgagag gagtccgact ggtggaagga attctgcatg     540
ccccagatgc tggctggggc aatctggtat atgttgtcaa ctatcccaaa gataacaaaa     600
ggaaaatgga tgagacagat gcttcctctg cagtgaaagt gaaaagagca gtccagaaaa     660
catctgacct catagtgttg ggtctcccct ggaaaacaac tgagcaggat ctgaaagact     720
atttcagtac ttttggagag gttcttatgg ttcaggtcaa gaaagatctt aaaactggtc     780
actcgaaagg gtttggcttt gttcgattta cagaatatga aacccaagtg aaagtaatgt     840
cacaacgaca tatgatagat gggcgatggt gtgactgtaa acttcccaac tctaagcaaa     900
gcccagacga gcctttgaga agcagaaagg tgtttgttgg acgttgtaca gaggacatga     960
ctgctgaaga gcttcagcag tttttctgtc agtatggaga agtggtagat gtcttcattc    1020
ccaaaccatt cagagctttt gccttcgtca cctttgcaga tgataaggtt gcccagtctc    1080
tttgtggaga ggatttgatc attaaaggaa tcagcgtgca tatatccaat gctgaaccta    1140
agcataaatg caatagacag ttagaaagaa gtggaagatt tggtggtaat ccaggtggct    1200
ttgggaatca gggtgggttt ggtaacagta gaggggtgg agctggcttg ggaaataacc    1260
agggtggtaa tatgggtgga gggatgaact ttggtgcttt tagcattaac ccagcgatga    1320
tggctgcggc tcaggcagcg ttgcagagca gttggggtat gatgggcatg ttagccagcc    1380
agcagaacca gtcgggccca tctgggaata ccaaagcca gggcagcatg cagagggaac    1440
caaatcaggc ttttggttct ggaaataatt cctacagtgg ttctaattct ggtgcccccc    1500
ttggttgggg gtcagcatca aatgcaggat cgggcagtgg ttttaatggg ggctttggct    1560
cgagcatgga ttctaagtct tctggctggg gaatgtaggt ggtgggggt ggttagtagg    1620 ttggttatta ggttaggtag atttagaatg gtgggattca aattttttcta aactcatggt    1680 aagtatattg taaaatacat atgtactaaa attttcagat tggtttgttc agtgtggagt    1740
atattcagca gtatttttga catttttctt tagaaaaaaa gagggaaag ctaaatgaat     1800 tttataagtt ttgttatata aagggttaaa atactgagtg ggtgaaagtg aactgctgtt    1860
tgcctaattg gtaaaccaac actacaattg atctcagaag gttctctgt aatattctat     1920 cattgaaatt gttaatgaat tctttgcatg ttcagagtag aaaccattgg ttagaactac    1980
```

```
attcttttct ccttatttta atttgaatcc caccctatga attttttcct taggaaaatc      2040
tccatttggg agatcatgat gtcatggtgt ttgattcttt tggttttgtt tttaacactt      2100
gtcttccttc atatacgaaa gtacaatatg aagccttcat ttaatctctg cagttcatct      2160
catttcaaat gtttatggaa gaagcacttc attgaaagta gtgctgtaaa tattctgcca      2220
taggaatact tctgtctaca tgctttctca tccaagaatt cgtcatcacg ctgcacaggc      2280
tgcgtctttg acggtgggtg ttccattttt atccgctact cttttatttca tggagtcgta      2340 tcaacgctat gaacgcaagg ctgtgatatg aaccagaag gctgtttgaa cttttgaaac       2400
cttgtgtggg attgatggtg gtgccgaggc atgaaaggct agtatgagcg agaaaaggag      2460
agcgcgtgca gagacttggt ggtggaaaat ggatattttt taacttggag agatgtgtca      2520
ctcaatcctg tggctttggt gagagagtgt gcagagagca atgatagcaa ataacgtacg      2580
aatgttttac atcaaaggac atccacatca gttggaagac tttgagtttt gttcttagga      2640
aacccacttt agttgaatgt gttaagtgaa atacttgtac ttccctcccc ctctgtcaac      2700
tgctgtgaat gctgtatggt gtgtgttctc ctctgttact gatctggaag tgtgggaacg      2760
tgaactgaag ctgatgggct gcgaacatgg actgagcttg tggtgtgctt gcaggagaa       2820 cttgaagca gagttcacca gtgagctcag gtgtctcaaa aagggtgga agttctcatg        2880 tctgttagct attcataaga atgctgtttg ctgcagttct gtgtcctgtg cttggatgct      2940
tttttataag agttgtcatt gttggaaatt cttaaataaa actgatttaa ataatatgtg      3000
tctttgtttt gcagccctga atgcaaagaa ttcatagcag ttaattcccc ttttttgaccc     3060 ttttgagatg gaactttcat aaagtttctt ggcagtagtt tatttttgctt caaataaact    3120 tatttgaaaa gttgtctcaa gtcaaatgga ttcatcacct gtcatgcatt gacacctgat      3180
acccagactt aattgctatt tgttcttgca ttgtccaaag tgaaagtttt tctttggttt      3240 gttttaatt tagttttttct taagtctggg tgaccgcacc taaaatggta agcagttacc      3300
ctctggcttg ttctgagtgc ctctgtgcat ttgattttct atttacatgc tgtataaatc      3360
tccactgggg aatcatgcct tctaaaaata tttgggagag ggcaaaagag ttgatttcta     3420
atgctttgta gcagagcata tcaatgggaa agaaggttaa gcaccttttct gtttgggatt    3480 tgaaaagtgg aattaattgc aatagggatg aagtagaaga aaccaagaaa ccatgtgcct     3540
gaaatacatt aagaagcctg attgatagct ttaagaacta gtagggtggg ttgtcttacc     3600
tgtggcagtc ttaagtgagg taggcttttg ccctcctgaa tgtgggggtt atgtagtgat     3660
gaatatgctc acaaaatcag attagactgt caatgcattg ttaatgtaaa agcaataata    3720
cattgattat tgtactttc ctgtaactac tgagaccgga ggcgctcctt ttctaactgg      3780
aagaatggga cagttttttgt gttggtagtt tttcctaatg cccttaccta aatagattat   3840
gataaatagg tttgtcattt tgcaagttgc gtgttttaaa atttatatc cgttagagac      3900 ttgttatgaa cacattgttt cattatacag tatcctctgt aaaaggatcg tgagttattg     3960 taagttttttt tctctgcatc taaccctgca tgatttccaa accctgtgca tctgaatttt    4020 gcatttagc actgtttgca ctgttactca gcagcagtaa catggtaaca ttaaaatggt     4080
tttcggggac ctccaaagac ggccaggagt cctggggtaa gttacttgtc aatggcatgg    4140
ttttgatccc ttttttacac ttgttaaaga cttactggtc atagaagtct ttcagtgttg    4200
atcagccttt taacatgttt atggatgaca tagctgtagt tagttacttg ccgtaaatga    4260
ggttttagaa ataaactact tggcaaagat ttggttttga aagtctggtc atcaaaacgc     4320
gttcattcct tagaaataat gaagaacaac tctttgaacc acagttgaat aaaaggttttt   4380
```

-continued

```
cttgccacca acagtttagt gtctggagtc ttactggaag aaaaaaaaat tctatatcat   4440
gacaatgcta gaaaagttaa ggtgacttat gtgggaagat gcaatatagc attttcatcc   4500
tttaaaattt gagtctccag gtgggtgtgg tggcccatgc ttttaatccc agaattggtg   4560
taaatgagtt gtaggccagc tatttcccca tcttgaggca ccctgtcttg ccttgttgga   4620
agagccagtt aaaatcaaac atgacccttta aggtcagcat cttagcagaa gagcagttta   4680
tttcaggata acttactgtt tttgatacat aagcaaatga ctgtaccttg tacagttacg   4740
gttgacttcc ctgagcccaa cgctcaccta agaaaagtgg gctgggtata gtgaaacacc   4800
tgttaaggtt tttggaatga tttgctaaat tgcccttgta aagggtaaaa tgctgtttcg   4860
tgttcttttt atctgacaat ttggtgaatc tggtagaaca tgcctatatc ccaatattct   4920
ggaatggact tggtgttaat ttaatagctg atcaatgtg aaggtcacac acctgctttc    4980
cgcttacctt ccaaaaggta ttctggaacc actcagaagt tactcagaaa gtaagagcac   5040
tttctgagct cattaagacc aaatctacac actagacaca acaagccctt tgttggccag   5100
aaatggaaac agccagtata aaataagtag attgtaggga atcaaataca acttgttttt   5160
tctgtgttgg gggttggcca agcactgtta aacacaaatc aaagctgata ttggcaagtg   5220
tttggacctg taacaatctc acctgctctg attttggggt aggctgtcat tcttaggttt   5280
gttactaagc ttcccaggta cttggcgata tgaggaacaa tgattggacg atgcaaatta   5340
gaaattactt attatgttct caatccaggg aatatagttg atgacttttg tgtagacccc   5400
atactggtct gccgcccac aattaatgga accccaggaa actattcctc ccacaaacca   5460
tcgctgtgtc tcattatcta gaaacactaa tgccccccca ctgtcacctc tgcagctgtc   5520
cttgccacca gtctctaagc cagcacagag catgttagcg cttactctta ctcctggata   5580
gagcttttca tacacggcgg tacattttg gtggtcagca attggtatgt ccacaaacat   5640
taggtttcta gcaagaagcc ccttctgggt taacccccag ccagccacag ttccagtgaa   5700
gtctgttctc attaaggatg cagcttcttt tcgcggtagg caaacaggca tgatgcttcc   5760
gttgattgtg actttgttct tgagtttaat caatgctata tcattgtcaa accagcacc    5820 gtgagtgtag ccttcatgta taaagatttc ctcgggccag gcttgagtgt aatgaggtga   5880
gagccttttg aggatgccca ttcggatgtt cagggaggac gctgccattc ttttctcata   5940
tacagcatga gcggctgtta ggacccaatt gtcatgtata agtgcacctg ctgctgctgt   6000
agtttgaccc agcaacaaga cttgccaagg aaagtcacca ggctttgcag gctgccctcc   6060
aactatgcgt cctcctatag tgtgtgtgga cagcccacaa actgagggat aaaaaacaag   6120
tatttaatgc cctacaaatt gataggcatc ctccctgttg agtgaggcta tttaagtttt   6180
tgtttagcct gctcacctcc ttgtaaagat cagtaagaga tctcagagat tgttttgctg   6240
aaagagaaca gcatgaggga gtctggacag gacttgtgtg caggaggaca tgacactact   6300
tagaggccaa agcaaccccc ctcaccacac cctgagctgc ttgttttct cttttttgggc     6360 tctctgggaa ttctgggaaa gcaggaacta tgatttacaa agtttctgtt gtctttaaat   6420
gtaagactct aaattacaat gttgcagcaa tagccaaagt gcttctggtt caaaaattgg   6480
taattttggt ctggtggagc cctccaaaca ctttaccgt tctttgcaaa ctgagggctc    6540
aggaatgcaa cacatgttct ttattgtggt tgtgcacttt gattaaaact tggaagccgc   6600
atgtcagcca aatacaaggc tagaaaacta atttaaacca gctaacacgg gggtaatgag   6660
tgtattatta cctttcaatt aaaaaaaaag cactctcaac tgttgttgga gccaattctg   6720
```

-continued

```
gtaaagaaat taagtacta ttaaaaggca aattgcatta atgtttaaaa atcttgatgt    6780
cgttgaaaac aattgcttag ggaaataatg aagttattag ctttgggggtt taatagcatt   6840 tttacagaga agaaaagtaa caagagttct tggttataaa tgtataaacg gtttgagata    6900
atttaagaaa tcatttaatt tttttatgctt gcctagttat aaggtcaaaa acaatcaagt   6960
gcatgatgca cctagcttcc gtgtggaagg ggaaatgtga gcacactgtt gggaaacact    7020
aagctccagc ctcagccaag tgctgagctt tctgcctccc cagccagacc ctgcctattg    7080
tctgccagct actctgtcag ctatgaatct cttttataaa tggcgtccat taccaggctc    7140
acaaaccggg gggagttttt ctcctttgga gctcgtccag aatccatcag cctcacacac    7200
atatttacct gcaagtcatt ggaaaagcaa aaatgtttag ctgtagttgt catttgcttg    7260
aataacccct tgaaaaatgt tgattcttga gcatctgtgg tggggagagg tgtgtgaata    7320 accatttttac atgatttcat aaataggtgt ctgcattacc atgtttgctt gcaaagtgga   7380 aacctttttag atgtgtaact tgaatatgta tcaagatctc aagtgcttaa tgataaggtt   7440
ttgacttgtt aaattaaacc atttggaata tattgtg                             7477
```

<210> SEQ ID NO 2
<211> LENGTH: 414
<212> TYPE: PRT
<213> ORGANISM: Mus musculus

<400> SEQUENCE: 2

```
Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Asp Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Pro Asp Glu Pro Leu Arg Ser Arg Lys
            180                 185                 190

Val Phe Val Gly Arg Cys Thr Glu Asp Met Thr Ala Glu Glu Leu Gln
        195                 200                 205

Gln Phe Phe Cys Gln Tyr Gly Glu Val Val Asp Val Phe Ile Pro Lys
    210                 215                 220

Pro Phe Arg Ala Phe Ala Phe Val Thr Phe Ala Asp Asp Lys Val Ala
225                 230                 235                 240
```

```
Gln Ser Leu Cys Gly Glu Asp Leu Ile Ile Lys Gly Ile Ser Val His
            245                 250                 255
Ile Ser Asn Ala Glu Pro Lys His Asn Ser Asn Arg Gln Leu Glu Arg
        260                 265                 270
Ser Gly Arg Phe Gly Gly Asn Pro Gly Gly Phe Gly Asn Gln Gly Gly
    275                 280                 285
Phe Gly Asn Ser Arg Gly Gly Ala Gly Leu Gly Asn Asn Gln Gly
    290                 295                 300
Gly Asn Met Gly Gly Met Asn Phe Gly Ala Phe Ser Ile Asn Pro
305                 310                 315                 320
Ala Met Met Ala Ala Gln Ala Ala Leu Gln Ser Ser Trp Gly Met
            325                 330                 335
Met Gly Met Leu Ala Ser Gln Gln Asn Gln Ser Gly Pro Ser Gly Asn
            340                 345                 350
Asn Gln Ser Gln Gly Ser Met Gln Arg Glu Pro Asn Gln Ala Phe Gly
        355                 360                 365
Ser Gly Asn Asn Ser Tyr Ser Gly Ser Asn Ser Gly Ala Pro Leu Gly
    370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met
            405                 410

<210> SEQ ID NO 3
<211> LENGTH: 5367
<212> TYPE: DNA
<213> ORGANISM: Homo sapiens

<400> SEQUENCE: 3
aaaccatctg ctacgttacg tgggggagg tcagctccta tacagccaca cttttttcaa      60
tcttcagctt ttcaggccta ggtcctggtt ttattttagc tttcagagct tctctgtagg    120
cttgaatttc caggaggcag cccgagtccc tggggagagg gtcatcgtgg ctctcgtcgg    180
tgccttccac ctctggacag caaccggtg ggagaggacg ccggtgggcg ggggaggag     240
gcggccctag cgccattttg tgggagcgaa gcggtggctg gctgcgctt gggtccgtcg    300
ctgcttcggt gtccctgtcg ggcttcccag cagcggccta gcgggaaaag taaagatgt    360
ctgaatatat tcgggtaacc gaagatgaga acgatgagcc cattgaaata ccatcggaag    420
acgatgggac ggtgctgctc tccacggtta cagcccagtt ccagggggcg tgtgggcttc    480
gctacaggaa tccagtgtct cagtgtatga gaggtgtccg gctggtagaa ggaattctgc    540
atgccccaga tgctggctgg ggaaatctgg tgtatgttgt caactatcca aaagataaca    600
aaagaaaaat ggatgagaca gatgcttcat cagcagtgaa agtgaaaaga gcagtccaga    660
aaacatccga tttaatagtg ttgggtctcc catggaaaac aaccgaacag acctgaaag     720
agtattttag taccttttgga gaagttctta ttggtgcaggt caagaaagat cttaagactg    780
gtcattcaaa gggggttggc tttgttcgtt ttacggaata tgaaacacaa gtgaaagtaa    840
tgtcacagcg acatatgata gatggacgat ggtgtgactg caaacttcct aattctaagc    900
aaagccaaga tgagcctttg agaagcagaa aagtgtttgt ggggcgctgt acagaggaca    960
tgactgagga tgagctgcgg gagttcttct ctcagtacgg ggatgtgatg gatgtcttca   1020
tccccaagcc attcagggcc tttgcctttg ttacatttgc agatgatcag attgcgcagt   1080
ctctttgtgg agaggacttg atcattaaag gaatcagcgt tcatatatcc aatgccgaac   1140
```

```
ctaagcacaa tagcaataga cagttagaaa gaagtggaag atttggtggt aatccaggtg    1200
gctttgggaa tcaggtggga tttggtaata gcagaggggg tggagctggt ttgggaaaca    1260
atcaaggtag taatatgggt ggtgggatga actttggtgc gttcagcatt aatccagcca    1320
tgatggctgc cgcccaggca gcactacaga gcagttgggg tatgatgggc atgttagcca    1380
gccagcagaa ccagtcaggc ccatcgggta ataaccaaaa ccaaggcaac atgcagaggg    1440
agccaaacca ggccttcggt tctgaaaata actcttatag tggctctaat tctggtgcag    1500
caattggttg gggatcagca tccaatgcag ggtcgggcag tggttttaat ggaggctttg    1560
gctcaagcat ggattctaag tcttctggct ggggaatgta gacagtgggg ttgtggttgg    1620
ttggtataga atggtgggaa ttcaaatttt tctaaactca tggtaagtat attgtaaaat    1680
acatatgtac taagaatttt caaaattggt ttgttcagtg tggagtatat tcagcagtat    1740
ttttgacatt tttctttaga aaaggaaga gctaaaggaa ttttataagt tttgttacat     1800
gaaaggttga atattgagt ggttgaaagt gaactgctgt ttgcctgatt ggtaaaccaa     1860
cacactacaa ttgatatcaa aaggtttctc ctgtaatatt ttatccctgg acttgtcaag    1920
tgaattcttt gcatgttcaa aacgaaaacc attgattaga actacattct ttacccctg    1980 ttttaatttg aaccccacca tatggatttt tttccttaag aaaatctcct tttaggagat    2040
catggtgtca cagtgtttgg ttcttttgtt ttgtttttta acacttgtct cccctcatac    2100 acaaagtac aatatgaagc cttcatttaa tctctgcagt tcatctcatt tcaaatgttt     2160
atggaagaag cacttcattg aaagtagtgc tgtaaatatt ctgccatagg aatactgtct    2220
acatgctttc tcattcaaga attcgtcatc acgcatcaca ggccgcgtct ttgacggtgg    2280
gtgtcccatt tttatccgct actctttatt tcatggagtc gtatcaacgc tatgaacgca    2340
aggctgtgat atggaaccag aaggctgtct gaacttttga accttgtgt gggattgatg     2400 gtggtgccga ggcatgaaag gctagtatga gcgagaaaag gagagagcgc gtgcagagac    2460
ttggtggtgc ataatggata tttttaact tggcgagatg tgtctctcaa tcctgtggct     2520
ttggtgagag agtgtgcaga gagcaatgat agcaaataat gtacgaatgt ttttgcatt    2580 caaaggacat ccacatctgt tggaagactt ttaagtgagt ttttgttctt agataaccca    2640
cattagatga atgtgttaag tgaaatgata cttgtactcc ccctaccct ttgtcaactg     2700 ctgtgaatgc tgtatggtgt gtgttctctt ctgttactga tatgtaagtg tggcaatgtg    2760
aactgaagct gatgggctga gaacatggac tgagcttgtg gtgtgctttg caggaggact    2820
tgaagcagag ttcaccagtg agctcaggtg tctcaaagaa gggtggaagt tctaatgtct    2880
gttagctacc cataagaatg ctgtttgctg cagttctgtg tcctgtgctt ggatgctttt    2940
tataagagtt gtcattgttg gaaattctta aataaaactg atttaaataa tatgtgtctt    3000
tgttttgcag ccctgaatgc aaagaattca tagcagttaa ttccccttttt ttgacccttt   3060 tgagatggaa ctttcataaa gtttcttggc agtagtttat tttgcttcaa ataaacttat    3120
ttgaaaagtt gtctcaagtc aaatggattc atcacctgtc atgcattgac acctgatacc    3180
cagacttaat tggtatttgt tcttgcattg gccaaagtga aaattttttt ttttcttttg    3240
aaatctagtt ttgaataagt ctgggtgacc gcacctaaaa tggtaagcag taccctccgg    3300 cttttttctta gtgcctctgt gcatttgggt gatgttctat ttacatggcc tgtgtaaatc   3360
tccattggga agtcatgcct tctaaaaaga ttcttatttg ggggagtggg caaaatgttg    3420
attattttct aatgctttgt agcaaagcat atcaattgaa aagggaatat cagcaccttc    3480
ctagtttggg atttgaaaag tggaattaat tgcagtaggg ataaagtaga agaaaccaca    3540
```

-continued

```
aattatcttg tgcctgaaat ccattaagag gcctgatagc tttaagaatt agggtgggtt      3600
gtctgtctgg aagtgttaag tggaatgggc tttgtcctcc aggaggtggg ggaatgtggt      3660
aacattgaat acagttgaat aaaatcgctt acaaaactca cactctcaca atgcattgtt      3720
aagtatgtaa aagcaataac attgattctc tgttgtactt ttttgtaact aattctgtga      3780
gagttgagct cattttctag ttggaagaat gtgatatttg ttgtgttggt agtttaccta      3840
atgcccttac ctaattagat tatgataaat aggtttgtca ttttgcaagt tacataaaca      3900
tttatcaatg aagtcatcct ttagacttgt aatcgccaca ttgtttcatt attcagtttc      3960
ctctgtaaag ggatcttgag ttgttttaat tttttttttc tgcatctgaa tctgcatgat      4020
ttccaaaccc tgtaccatct gaattttgca ttttagcact tgcactatta ctcagcagca      4080
gtaacatggt aacacttaaa atggtactcg gggacctcca aagactaaac tgacaagcct      4140
tcaaggagcc caggggtaag ttaacttgtc aacggcatgg tttaatccct tctttacact      4200
tgtgtaaatt tcagttactg gtcatagaag gctttcaatg ttgagtggcc ttttattaac      4260
atgtttatgg tactgcatag atacgggtat ttattttacc ctaagaagat tttgaagttt      4320
aaaagtactt aaactatttg gcaaagattt gttttttaaaa atctatttgg tcaatctaaa      4380
tgcattcatt ctaaaaaatt ttttgaacca gataaataaa atttttttt gacaccacag      4440 tttagtgtct ggagtcttac tggaaaaaca cgatttcttt ttatatgtga tatacagatg      4500
ctggaaagtt acctttaaaa attgagtctc taaagaaaaa agaaataat aaaaattgag      4560 tctcaagaag ttgtacttca tatgcacaag agaaatgagg ccaagactca cagtaagctt      4620
ttacatggaa tggtaacttt tagttagact gaaaaacttg aatgttagct attaaaacct      4680
tttaggaagg aatagccagc taaaaccaaa tgagattttt aaagttaaat cagcacttaa      4740
gttgtgtcct tagtaggaaa aagtaggaag ttaactactc cgtaatccaa gagataatgt      4800
gtaacagtaa gaatgatttt gttgttgttg agtatgagca aagtagcccc taagtgtgta      4860
ttagggttct gtacttaact gttgtgtgat gtgtgctttt gttaggcatc actgtgccca      4920
agtatttcat gttcattgta aagaggaaaa atacagattt ctctataatg tcaccactta      4980
tttctaatgc cacttttcat cttgtggaaa tgccatgttt tgattcagtc ttctgaattt      5040
gaacattatt caggttattt ccaattgctg ggaatatcct tactgctaaa ataaattctt      5100
agcattggaa ttgctaggtc aaagattatg catgcttttt aagggctttt gaaatgtatt      5160
gccagtctgt ggcctgccac cctccctgaa catgcctggt cttgcttaaa atgtattgcc      5220
aaatagtcct tgggaagttt atgttgtctt taacaatgtg aaatagtact actattcacg      5280 ttcctttgt ctgacaattt gataagtgaa taattgtatc ccaccattct gtagtattgg      5340
tttttaacat ggaaattta gtcaata                                          5367
```

<210> SEQ ID NO 4
<211> LENGTH: 414
<212> TYPE: PRT
<213> ORGANISM: Homo sapiens

<400> SEQUENCE: 4

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

-continued

Gln Cys Met Arg Gly Val Arg Leu Val Glu Gly Ile Leu His Ala Pro
 50                  55                  60

Asp Ala Gly Trp Gly Asn Leu Val Tyr Val Asn Tyr Pro Lys Asp
 65                  70                  75                  80

Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 5
<211> LENGTH: 24
<212> TYPE: DNA
<213> ORGANISM: Artificial Sequence
<220> FEATURE:
<223> OTHER INFORMATION: PCR forward primer

<400> SEQUENCE: 5

```
gacctcaact gctctgcttc tacc                                          24

<210> SEQ ID NO 6
<211> LENGTH: 22
<212> TYPE: DNA
<213> ORGANISM: Artificial Sequence
<220> FEATURE:
<223> OTHER INFORMATION: PCR reverse primer

<400> SEQUENCE: 6
aacggaatca atcctctcca gg                                            22

<210> SEQ ID NO 7
<211> LENGTH: 18
<212> TYPE: DNA
<213> ORGANISM: Artificial Sequence
<220> FEATURE:
<223> OTHER INFORMATION: Tardbp forward primer

<400> SEQUENCE: 7
ggtaatccag gtgctttg                                                 18

<210> SEQ ID NO 8
<211> LENGTH: 20
<212> TYPE: DNA
<213> ORGANISM: Artificial Sequence
<220> FEATURE:
<223> OTHER INFORMATION: Tardbp reversed primer

<400> SEQUENCE: 8
cctgcatttg atgctgaccc                                               20

<210> SEQ ID NO 9
<211> LENGTH: 22
<212> TYPE: DNA
<213> ORGANISM: Artificial Sequence
<220> FEATURE:
<223> OTHER INFORMATION: Bcl-2 splicing forward primer

<400> SEQUENCE: 9
ttcggggaag gatggcgcaa gc                                            22

<210> SEQ ID NO 10
<211> LENGTH: 24
<212> TYPE: DNA
<213> ORGANISM: Artificial Sequence
<220> FEATURE:
<223> OTHER INFORMATION: Bcl-2-201 forward primer

<400> SEQUENCE: 10
acggaggctg ggatgccttt gtgg                                          24

<210> SEQ ID NO 11
<211> LENGTH: 21
<212> TYPE: DNA
<213> ORGANISM: Artificial Sequence
<220> FEATURE:
<223> OTHER INFORMATION: Bcl-2 reversed primer

<400> SEQUENCE: 11
tcacttgtgg cccaggtatg c                                             21

<210> SEQ ID NO 12
<211> LENGTH: 35
<212> TYPE: DNA
```

```
<213> ORGANISM: Artificial Sequence
<220> FEATURE:
<223> OTHER INFORMATION: PCR forward primer

<400> SEQUENCE: 12
ccgctcgagc ggatgtctga atatattcgg gtaac                              35

<210> SEQ ID NO 13
<211> LENGTH: 31
<212> TYPE: DNA
<213> ORGANISM: Artificial Sequence
<220> FEATURE:
<223> OTHER INFORMATION: PCR reverse primer

<400> SEQUENCE: 13
tgctctagag cacattcccc agccagaaga c                                  31
```